United States Patent [19]
de la Huerga

[11] Patent Number: 5,852,590
[45] Date of Patent: Dec. 22, 1998

[54] INTERACTIVE LABEL FOR MEDICATION CONTAINERS AND DISPENSERS

[76] Inventor: Carlos de la Huerga, 9190 N. Upper River Rd., River Hills, Wis. 53217

[21] Appl. No.: 832,613

[22] Filed: Mar. 28, 1997

Related U.S. Application Data

[60] Provisional application No. 60/033,491, Dec. 20, 1996.

[51] Int. Cl.⁶ ................................................. G04B 37/00
[52] U.S. Cl. .............................................................. 368/10
[58] Field of Search ........................... 368/107–113, 10, 368/108; 221/2, 3, 15; 340/309.4; 364/569

[56] References Cited

U.S. PATENT DOCUMENTS

| | | | |
|---|---|---|---|
| 3,227,127 | 1/1966 | Gayle | 116/121 |
| 4,207,992 | 6/1980 | Brown | 221/15 |
| 4,360,125 | 11/1982 | Martindale et al. | 221/2 |
| 4,437,579 | 3/1984 | Obland | 221/25 |
| 4,483,626 | 11/1984 | Noble | 368/10 |
| 4,504,153 | 3/1985 | Schollmeyer et al. | 368/10 |
| 4,526,474 | 7/1985 | Simon | 368/10 |
| 4,573,606 | 3/1986 | Lewis | 221/2 |
| 4,616,316 | 10/1986 | Hampeter | 364/413 |
| 4,617,557 | 10/1986 | Gordon | 340/568 |
| 4,626,105 | 12/1986 | Miller | 368/10 |
| 4,674,651 | 6/1987 | Scidmore | 221/3 |
| 4,695,954 | 9/1987 | Rose et al. | 364/413 |
| 4,725,997 | 2/1988 | Urquhart et al. | 368/10 |
| 4,811,764 | 3/1989 | McLaughin | 141/98 |
| 4,939,705 | 7/1990 | Hamilton et al. | 368/10 |
| 4,953,745 | 9/1990 | Rowlett | 221/5 |
| 4,984,709 | 1/1991 | Weinstein | 221/7 |
| 5,047,948 | 9/1991 | Turner | 364/479 |
| 5,088,056 | 2/1992 | McIntosh et al. | 364/569 |
| 5,099,463 | 3/1992 | Lloyd | 368/10 |
| 5,181,189 | 1/1993 | Hafner | 368/10 |
| 5,213,232 | 5/1993 | Kraft et al. | 221/227 |
| 5,233,571 | 8/1993 | Wirtschafter | 368/10 |
| 5,313,439 | 5/1994 | Albeck | 368/10 |
| 5,347,453 | 9/1994 | Maestre | 364/413 |
| 5,392,952 | 2/1995 | Bowden | 221/15 |
| 5,408,443 | 4/1995 | Weinberger | 368/10 |
| 5,472,113 | 12/1995 | Shaw | 221/7 |
| 5,522,525 | 6/1996 | McLaughlin et al. | 221/4 |

*Primary Examiner*—Bernard Roskoski
*Attorney, Agent, or Firm*—Sokol Law Office

[57] ABSTRACT

This invention relates to a multi-piece, automated medication container having a first piece with an interactive label and a machine readable and writable electronic memory strip. The memory strip contains prescription information, medication information and program codes that are downloaded to a second piece having a computer processor. In one embodiment of the invention, the interactive label is affixed to a vial of a standard childproof container. The vial is sealed by an automated cap. The automated cap includes sensors for reading the information and codes on the memory strip and a memory for storing the information and codes. The automated cap also includes a display for visually or audibly indicating desired information to the patient, such as when to take the next dose of medication. A computer controlled locking assembly in the cap presents its removal before the prescribed time for taking the next dose of medication. The sensors also obtain actual medication consumption information based on when the container is opened. This actual consumption information is used to keep inventory information regarding the number of doses remaining in the container. The actual consumption information and inventory information is stored in the memory of the cap or sent to the interactive label to update the memory strip. The memory strip can also contain contraindication information for downloading to a personal home computer or a hospital or nursing home computer. In an other embodiment, the interactive label is affixed to a blister pack containing individual doses of medication. The blister pack is then placed in an automated dispenser.

60 Claims, 11 Drawing Sheets

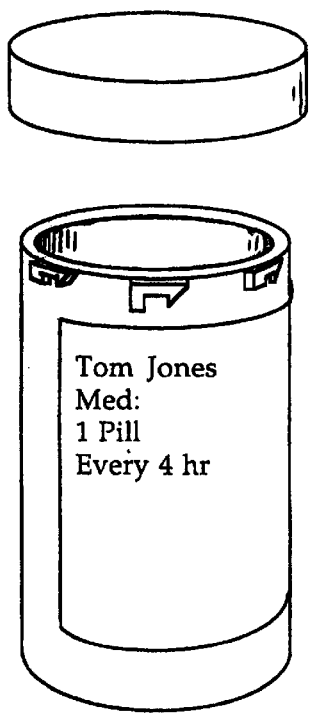
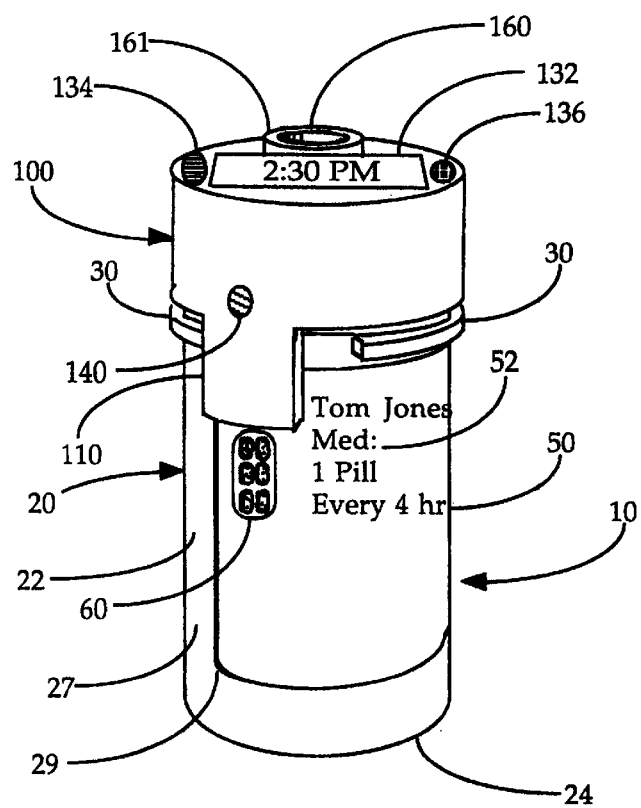
Figure 1 (PRIOR ART)
Figure 2

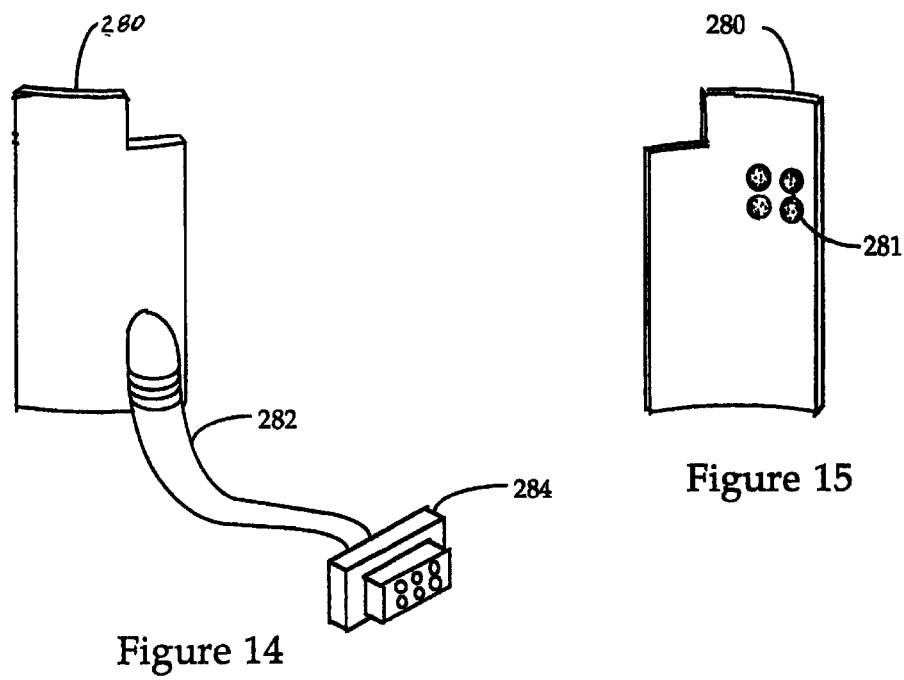
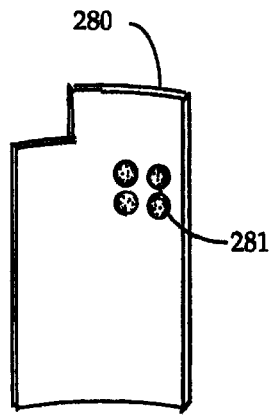
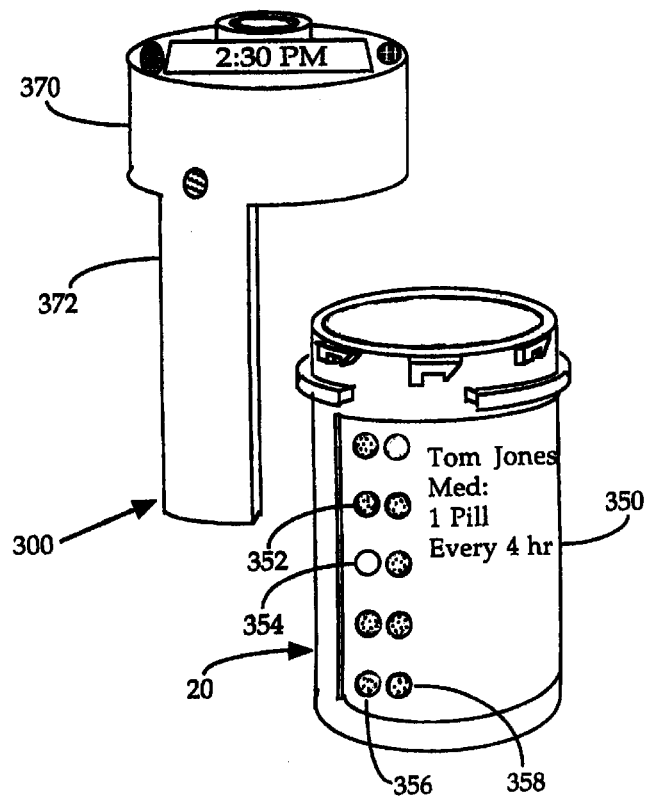
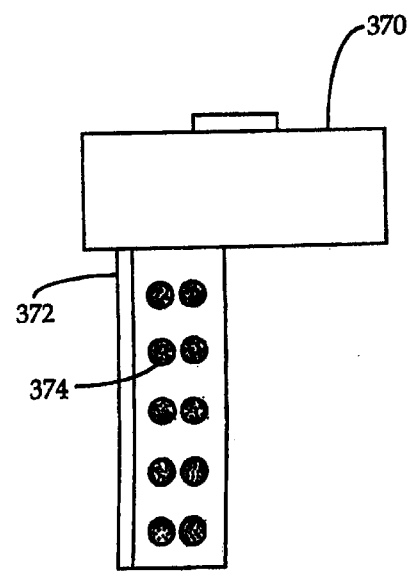
Figure 14
Figure 15
Figure 16
Figure 17

INTERACTIVE LABEL FOR MEDICATION CONTAINERS AND DISPENSERS

This application claims benefit of USC Provisional Application No. 60/033,491 filed Dec. 20, 1996.

TECHNICAL FIELD

This invention pertains to a multi-piece medication container having a first piece with an interactive label and memory strip containing prescription information, medication information and program codes that are downloaded to a second piece having a computer processor for communicating information to a patient and inputting or updating information in the memory strip.

BACKGROUND

Medication containers that remind a patient to take their medication or keep track of the number of doses of medication in the container are well known. Examples of such automated containers are disclosed in U.S. Pat. No. 3,227,127 (Gayle); 4,207,992 (Brown); 4,360,125 (Martindale); 4,483,626 (Noble); 4,504,153 (Schollmeyer); 4,526,474 (Simon); 4,573,606 (Lewis); 4,695,954 (Rose); 4,725,997 (Urguhart); 4,939,705 (Hamilton); 4,984,709 (Weinstein); 5,099,463 (Lloyd); 5,181,189 (Hafner); 5,213,332 (Kraft); 5,313,439 (Albeck); 5,392,952 (Bowden); 5,472,113 (Shaw) and 522,525 (McLaughlin), the disclosures of which are incorporated by reference.

The general purpose of an automated container is to improve patient compliance in taking medication on schedule. While taking medication on a regular schedule may seem a simple process, it is often difficult to accomplish, especially if the medication or an illness causes the person to think less clearly or to be forgetful. There is the anxiety of being uncertain if you took the medication earlier in the day. Then, there is the problem of patients completely forgetting to take their medication. The first condition is alleviated by simply indicating when the medication is to be taken next. If the container indicates a future time or day to take the next medication, the patient knows that they have taken the current dosage. If the container indicates a present or past time, the patient knows that they should take the medication now. To solve the problem of completely forgetting to take a dosage of medication, a container will typically contain an alarm to remind the patient to take the medication. Unfortunately, the presently available products and the above patents suffer from one or more problems or limitations.

One problem in reminding patients to take their medication on time is that many automated medication systems are not transportable. This is especially true of systems that handle complicated dosing regimes, handle a variety of medications, or provide fairly detailed information about the medications being consumed. Yet, many patients are not home bound. In fact, the purpose of many medications is to enable people that would otherwise be incapacitated to live normal, ambulatory lives. To be effective, medication alerting methods must be easily transportable, not just an in-home alarming system.

An additional problem is childproofing the automated medication container. Childproofing is frequently necessary to prevent an infant, child, or mentally handicapped or medicated person from gaining unsupervised access to the medication. The childproofing features must cooperate with the automated features of the container.

A further problem is that some automated dispensers dispense a variety of different pills at the same time. Some dispensers empty a preloaded number of pills from the container as it passes over an open dispensing chute. If the patient does not take all the medication, there is no place to put the excess. The medication either remains in the dispensing area, possibly resulting in an accidental overdose at a later time or consumption by a child, or the medication is thrown out. If an attempt is made to reload the medication into the dispenser, the dispensing patterns can be inadvertently altered. This is particularly problematic if the dispenser is handling medications that are similar in appearance.

A still further problem is that errors can occur when a care giver removes a variety of medications from the pharmacist supplied containers and inserts the medications into a different medication container or machine. An example being a container with separate compartments marked "breakfast, lunch and dinner", or "Monday, Tuesday, Wednesday, etc." In fact, there is some question regarding the legality of a care giver removing medications from pharmacist supplied containers and placing them into other containers. There is good reason for caution regarding the shuffling of medication from one container to another. Given the strength of many medications in use today, any confusion about the medications put in the secondary container or any confusion regarding the prescription regimens could have a significant adverse affect on the patient.

A still further problem is that the patient must program a timing or alarming mechanism in an automated dispenser by manual entry of additional coded data. A magnetic strip or smart card can also be used to enter the data. Unfortunately, the cards are easily misplaced and errors can result if the wrong data is entered into the dispensing machine manually or via an incorrect card. In addition, such dispensing machines have to be returned to the pharmacist frequently for reprogramming when a new medication is prescribed.

A still further problem is that many medication containers do not provide a means for counting the number of pills remaining in the container or the number of pills taken to date. The patient or care giver must manually enter the amount of medication dispensed or account for the quantity of medication remaining after each dose is consumed. In situations where the unused portion of a prescribed medication is returned to the pharmacy, such as in a hospital setting, the pharmacist must manually count the number of pills left in the container.

A still further problem with conventional automated medication containers is that they do not record the actual dosing regimen taken by the patient. A patient could take the medication too early, too late or completely miss taking the medication at various times. This results in a sporadic actual consumption or dosing regimen for the medication. The containers in use today do not provide an easy method of communicating the sporadic extent of the actual consumption regimen to the patient, or their pharmacist or physician.

A still further problem in designing an automated medication container is that the container should be compatible with conventional, non-automated medication containers used by the pharmaceutical industry today. See FIG. 1. A dramatic deviation from the conventional design would inhibit the adoption of the automated container design. A compatible design would enable the pharmacist to continue using conventional, non-automated containers in situations where such a container is appropriate, but would enable the pharmacist to provide an automated container in situations where this type of container is appropriate.

A still further problem with designing an automated medication container is that the more expensive automated components should be reusable. The increased cost of providing a microprocessor, memory displays, alarms and circuitry in a container would likely be prohibitive if the entire container disposed of after a single prescription is consumed. As many components as possible must be designed to be reused.

The present invention overcomes these and other limitations in existing medication dispensing products.

SUMMARY OF THE INVENTION

This invention relates to a multi-piece, automated medication container having a first piece with an interactive label and machine readable and writable, electronic memory strip. The memory strip contains prescription information, medication information and program codes that are downloaded to a second piece having a computer processor. In one embodiment of the invention, the interactive label is affixed to a vial of a standard or slightly modified childproof container. The vial is sealed by an automated cap. The automated cap includes sensors for reading the information and codes on the memory strip and its own memory for storing the information and codes. The automated cap also includes a display for visually or audibly indicating desired information to the patient, such as when to take the next dose of medication. A computer controlled locking assembly in the cap prevents its removal before the prescribed time for taking the next dose of medication. The sensors also are provided to obtain actual medication consumption information based on when the container is opened. This actual consumption information is used to keep inventory information regarding the number of medication doses remaining in the container. The actual consumption information and inventory information is stored in the memory of the cap or sent to the interactive label to update the memory strip. The memory strip can also contain contraindication information for downloading to a personal home computer or a hospital or nursing home computer. In an other embodiment, the interactive label is affixed to a blister pack containing individual doses of medication. The blister pack is then placed in an automated dispenser.

One advantage of the present invention is that the interactive label contains a wide variety of information that is not practical to print out in textual form on a relatively small label. The memory or memory strip contains information regarding the number of pills or capsules to be taken per dosage and the dosing regimen, e.g. daily, four times a day, before a meal, etc. The memory strip also contains information regarding the medication, such as the medication name, expiration date, quantity in container, patient name, pharmacy name, address and telephone number, pharmacy prescription number, prescribing doctor name and telephone number.

Another advantage of the present invention is that the memory strip contains special prescription requirements and instructions that are expressed in the form of a series of processor instructions such as those written in the Java or other computer language, as opposed to a simple four times per day dosing regime. The prescription requirements can, for example, indicate frequent dosages of a medication when starting a medication, then indicate a gradual reduction of medication, and finally indicate a sustained steady dose after several days.

A further advantage or the present invention is that the memory strip can contain prescription requirements that include instructions for alternating between differing medications in a controlled sequence. For example, some advances in Acquired Immune Deficiency Syndrome (AIDS) medication protocols require the patient to consume two or more medications, but on alternating or sequential days. Although each medication is held in a separate container, the memory strip on each medication container could provide instructions on taking both medications.

A still further advantage of the present invention is that the interactive label is compatible with the vials used in standard or slightly modified pharmacist supplied medication containers. Special vials are not necessary. Medication can be inserted in standard or slightly modified pharmacist supplied container and a memory strip affixed to the vial. Patients can then replace the standard cap for the container with an automated cap to obtain the information in the memory strip.

A still further advantage of the present invention is that the interactive label can provide sufficient information to enable a single container to hold and dispense a variety of medications. Although the medications would have to be sufficiently different looking in appearance to avoid confusion, the memory strip can provide enough detailed information to provide the patient with instructions for taking all the types of medication in the container. Such a medication container would alleviate the need for the patient to carry around several containers at once.

A still further advantage of the present invention is that the memory strip can be secured to a container via the use of a textual label or the strip can be secured directly to the medication container itself. The memory strip need not be secured to a label. This flexibility facilitates the use of the memory strip on a variety of containers depending on the intended function and manufacturing costs of the container.

A still further advantage of the present invention is that actual medication consumption information can be downloaded into the memory strip. This enables the patient to keep the more expensive automated cap, and return the vial and memory strip to the pharmacist or physician for analyzing the patient's response to and the effectiveness of the medication. The pharmacist or physician can read the information on the memory strip via a separate sensing element kept in their office.

A still further advantage of the present invention is that the microprocessor, memory sensors, display and alarms are located in the cap of the container. The memory strip is affixed to the container vial. This enables a patient to reuse the automated cap for different prescriptions. The vial and the memory strip which contains information specific to the prescription for the medication in the container can be discarded or returned to the pharmacist or physician. The more expensive automated cap is reused for subsequent prescriptions, thereby reducing the long term cost of the automated container.

A still further advantage of the present invention is that the information in the interactive label and the microprocessor memory is used to alert the patient when it is time to take a dose of medication and how many pills or capsules to consume. The interactive label and microprocessor are also used to warn the patient to defer taking medication at the present time, or indicate at what time the next dose of medication is to be taken. These alarms and indicators should increase patient compliance in taking medication according to the prescribed regimen.

A still further advantage of the present invention is that the automated medication container can convey information to a separate device such as a patient's home computer to aid in alerting the patient to take the medication in a timely manner. For example, the patients' home computer can page the patient when it is time to take a dose of medication.

A still further advantage of the present invention is that the interactive label and automated cap are compatible with a conventional medication container having a cylindrical vial and childproof cap. See FIG. 1. The pharmacist can dispense medication in a standard or slightly modified childproof container affixed with the interactive label. The patient is then free to replace the conventional childproof cap with an automated childproof cap.

The conventional medication vial can be easily modified to facilitate use with the interactive label. The slightly modified vial includes a guide and limiting ring molded around the periphery of the vial. The interactive label is aligned with an opening in the ring. A sensing tab in the cap extends through the opening in the ring and over the contacts for the memory strip. The ring ensures the unique placement of a sensing tab when the appropriate automated cap is secured to the vial. When properly closed, the sensing tab electronically reads the electronic memory strip. The ring does not interfere with the operation of the standard commercially available cap or the automated childproof cap.

A still further advantage of the invention is that the automated cap includes a battery or photo cell, a microprocessor with a timing circuit, and a LCD display. The timing circuit enables the cap to provide the time of day, day of the week or date to the patient.

A still further advantage of the present invention is that the medication container checks to ensure that the patient secured the automated cap to its corresponding vial. When the automated cap is attached to a vial having an interactive label, a check is made to determine if the cap was previously attached to this vial by comparing the prescription information now being sensed and read to the information previously stored in the memory of the microprocessor in the cap. If the information is the same as previously recorded, a notation is made that the patient probably just consumed a dosage of the medication and the timing program is adjusted to alert the patient to take the next dose after the appropriate time passes. If the information is different from that previously recorded, the patient is alerted to the possibility that the cap has been placed on the wrong medication container. The patient can then remove the cap and place it on the correct container. Alternately, the patient can ignore the alert and allow it be to automatically canceled after a time period passes or can manually cancel the alert by pressing a button on the cap. In each case, the new information is copied into the internal memory of the automated cap and an indication is made to the patient that they can take the medication according to the present memory strip prescription instructions.

An additional advantage of the present invention is that it can be used to record actual medication consumption information. The timing circuit enables the automated cap to obtain actual consumption information by recording when the cap is removed from the medication vial. Removal of the cap disrupts the alignment of the sensing tab with the contacts of the memory strip. This disruption or returning the cap to seal the vial establishes the time and date the user consumed the medication. The prescription timing regimen is used to compute the next time the patient should take the medication. When the cap is replaced and the information in the memory strip matches the information previously recorded into the memory of the microprocessor, the microprocessor determines that the user just removed the cap, consumed a dose of medication, and replaced the cap.

A still further advantage of the present invention is that the cap computes the next time the patient is to take the medication and displays this information to the patient. The time and or date or day is displayed via a display such as a LCD device in the cap. By reading the display, the user can easily and reliably determine the next time to take the medication. The LCD display includes the number of pills or capsules to be consumed. Given enough display area, specific instructions for taking the medication will be presented, e.g., "consume 2 hours before eating."

A still further advantage of the present invention is that the cap can alert the patient to take the medication by sounding an audible alarm, illuminating an indicator such as an LCD, or rotating an eccentrically positioned weight to cause a vibration alert. These alarms should improve patient compliance.

A still further advantage of the present invention is that prescription information on the memory strip is conveyed to the patient's personal home computer, or a hospital or nursing home computer. The information on the memory strip controls additional alerting means, such as additional light sources, audible alarms, via telecommunication to call the patient at home or office depending on the time of day to remind the patient to take the medication. The patient can respond by using the telephone keypad to indicate whether a dose was taken. In this way, patient compliance with the physician prescription can be tracked. Alternately, the personal home computer can page the patient to indicate which medication is to be taken. The memory strip information is copied to the home or business personal computer via a separate sensing element capable of communicating with the personal or business computer. The container can also be equipped with an infrared transmitter activated by the patient to send the memory strip information to the personal computer.

A still further advantage of the present invention is that the childproof container helps prevent the patient from taking medication too soon or too frequently. The cap is equipped with a locking mechanism that interacts with the childproof locking features. When the cap is in place, a solenoid activated armature prevent any attempt to open the cap until the appropriate time for taking the medication. When it is time to consume the medication, the solenoid releases the armature. The locking mechanism can also limit the number of times a day the patient can gain access to medication that is consumed on an as needed basis, e.g. medication used to control pain. This helps prevent the patient from taking the medication too many times in any given day or from repeating dosages of the medication within too short a time period.

A still further advantage of the present invention is that the interactive label is compatible with a multi-dose blister pack. The blister pack can be prepackaged by the original manufacturer or by a local pharmacy. The interactive label is then affixed to a surface of the blister pack. The label includes the memory strip and textual information regarding the medication prescription.

A still further advantage of the present invention is that the blister pack and interactive label can be inserted into a dispenser having a compatible sensing element, microprocessor, memory sensors, optional alerting device LCD display. This dispenser alerts the patient when to take medication, helps ensure that the medication is not accessible to a child (childproof), prevents the patient from taking too much medication or taking it prematurely, and indicates when the medication supply is being exhausted to allow the patient adequate time to obtain a refill of the prescription. The dispenser also includes a mechanism for assisting the patient in dispensing the medication from the blister pack.

Other advantages and aspects of the invention will become apparent upon review of the specification, claims and drawings.

BRIEF DESCRIPTION OF THE DRAWINGS

FIG. 1 is a perspective view of a conventional, childproof, medication container consisting of a cylindrical vial and a removable cap.

FIG. 2 is a perspective view of a first embodiment of the present invention where the medication container includes a cylindrical vial with an interactive label having an electronic memory strip, and an automated cap that seals the open end of the vial.

FIG. 14 is a front perspective view showing a sensing device used to convey information in the memory strip of the medication container to a separate computer.

FIG. 15 is a rear perspective view of the sensing device showing the sensors that engage the electrical contacts of the memory strip.

FIG. 16 is a perspective view of a third embodiment of the present invention where the medication container includes a cylindrical vial with an interactive label having a plurality of conductive or reflective surfaces, and an automated cap that seals the open end of the vial.

FIG. 17 is an elevation view of the automated cap for the third embodiment of the invention showing a plurality of sensors on the inside of the cap that sense the conductive or reflective surfaces of the interactive label.

DETAILED DESCRIPTION

Figure 3:
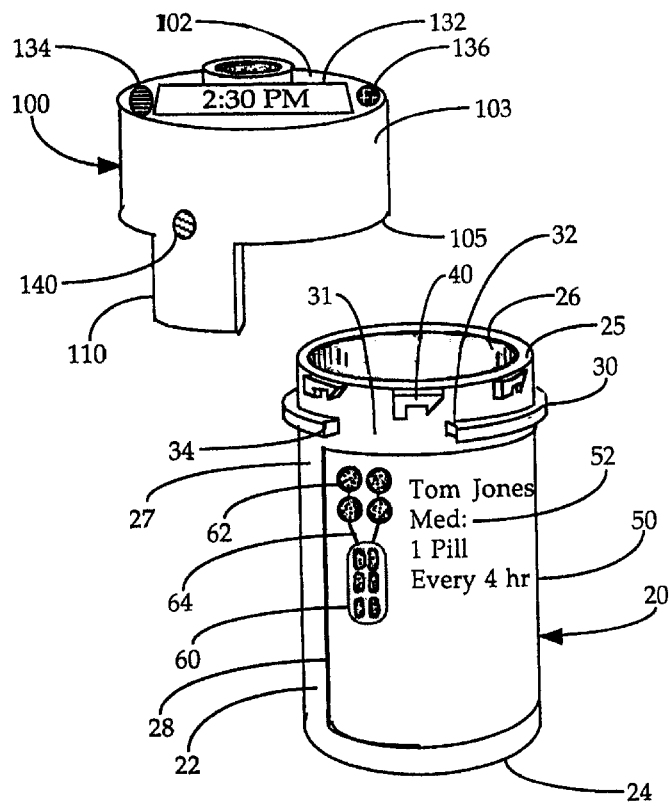
FIG. 3 is a perspective view of the first embodiment of the invention showing the automated cap removed from the vial to reveal the electrical contacts of the memory strip

The present invention relates to a medication container with an interactive label. While the invention is susceptible of embodiments in many different forms, there are shown in the drawings and will herein be described, several forms of the invention with the understanding that the present disclosure is to be considered as an exemplification of the principles of the invention, and is not intended to limit the broad aspects of the invention to the several embodiments illustrated.

First Embodiment

Figure 4:
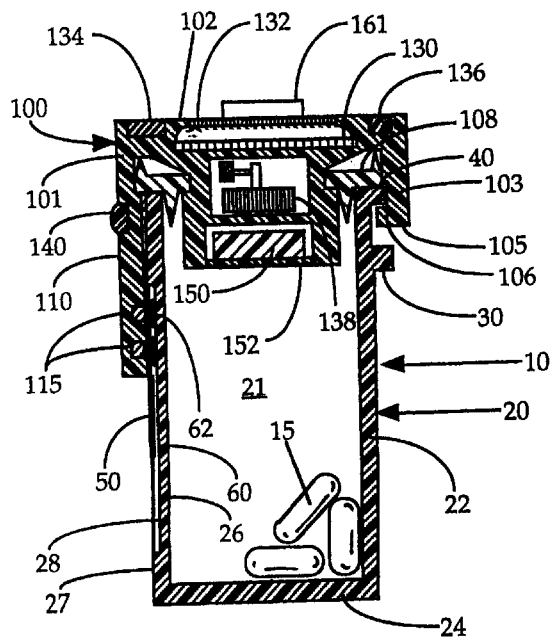
FIG. 4 is a cross sectional, side plan view of the first embodiment of the invention showing the electronic memory strip and its electrical contacts on the wall of the vial, and an automated cap with a resilient sealing disc, battery, audio, illuminating and vibrational alarms.

FIGS. 2–11 show a first embodiment of the invention where the container 10 includes a vial 20 with an interactive label 50 and an automated cap 100 with a sensing tab 110 for reading the electronically stored information 80 on the label and a computer processor 120 for controlling a visual display and a variety of alarms. As best shown in FIGS. 2–4, the vial 20 includes a compartment 21 defined by a cylindrical wall 22, a closed bottom end 24 and an open top end 25. Medication 15 is inserted into and removed from the compartment 21 via the open end 25 of the vial 20. The cylinder has an inner surface 26 and an outer surfaces 27. The vial 20 is made of a unitary piece of relatively rigid plastic similar to other conventional vial-type medication containers.

The vial 20 includes a first means for aligning the interactive label 50 with a predetermined location of the wall 22. This alignment means is accomplished by forming a recess 28 in the outer surface 27 of the wall 22. The recess 28 is defined by an inwardly projecting ridge 29 that extends around the perimeter of the recess. While this first alignment means is shown as recess 28, it should be understood that it could take on a variety of forms. For example, an outwardly projecting ridge (not shown) protruding from the wall 22 of the vial 20, or a raised substantially flat platform (not shown) protruding from the wall could be used. It should also be understood that the label 50 could be located on the inside surface 26 of the vial 20 without departing from the broad aspects of the invention.

The vial 20 includes a second or means for aligning the automated cap 100 with the vial 20 so that the sensing tab 110 of the cap is properly aligned with the interactive label 50 as discussed below. The second alignment means is accomplished by a guide ring 30 protruding from the outer surface 27 of the vial 20. The guide ring 30 is located at a substantially uniform, predetermined distance from the open end 25 of the vial. The guide ring surrounds most of the wall 22 of the vial. The guide ring has an opening 31 defined by its two ends 32 and 34. The ends 32 and 34 of the guide ring 30 are spaced apart a predetermined distance so that opening 31 has a predetermined size for accommodating sensing tab 110 as discussed below. While the second alignment means is shown and described as being guide ring 30, it should be understood that the second alignment means could take on other forms without departing from the broad aspects of the invention.

The vial 20 has several securement ratchets 40 for securing and sealing the cap 100 against the open end 25 of the vial. The ratchets 40 are evenly spaced around the open end 25, and protrude from the outer surface 27 of the vial 20. The ratchets are similar to those found on conventional child-proof medication containers as in FIG. 1. Each ratchet include a cup portion 42, a top surface 44, a wedge 45 and a side surface 46. Although the ratchets 40 are shown and described as being evenly spaced from each other as in a conventional vial, it should be understood that one or more of the ratchets could be offset. Such an offset arrangement could be used to accomplish the second alignment means in lieu of guide ring 30.

Figure 5:
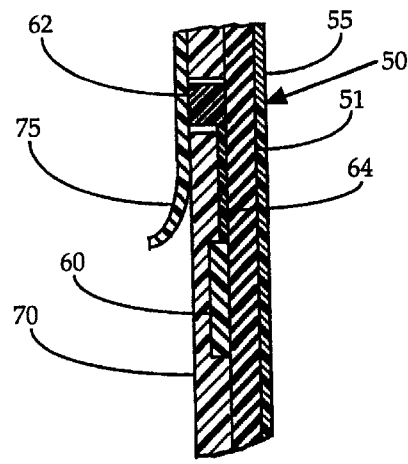
FIG. 5 is an enlarged, cross-sectional, side plan view of the interactive label showing the memory strip, electrical contacts, adhesive coating, protective coating and removable insulating layer.

As best shown in FIGS. 3–5, medication container 10 includes interactive label 50. The label 50 is affixed in the recess 28 in the wall 22 of the vial 20 so that the left edge of the label abuts and is aligned with the ridge 29 forming the left side of the recess. The upper edge of the label 50 abuts the ridge forming the upper side of the recess 28. This alignment positions the label 50 into its desired location on the wall 22 of the vial 20.

The interactive label 50 includes a paper backing 51 sized to fit in recess 28. The front surface of the paper backing 51 has a textual portion 52. The textual portion 52 includes textual information such as the patient's name, the medication name, the dosing regimen (e.g., daily, four times a day, etc.), the number of pills or capsules to consume during each dose, and any special instructions regarding the proper consumption of the medication (e.g., take an hour before meals). The rear surface of the backing paper 51 includes an adhesive coating 55 for affixing the label in the recess 28 of the wall 22 of the vial 20.

The interactive label 50 includes an electronic, machine readable and writable memory strip 60. The memory strip 60 is similar to those used in commercially available smart cards. The memory strip 50 includes contacts 62 that are in electrical communicate with the information 80 in the memory strip 60 via links or electrical connections such as wires 64 as discussed below. A protective coating 70 is applied over the memory strip 60. The protective coating 70 has holes aligned over each electrical contact 62. A removable insulating layer 75 is used to prevent premature communication with the memory strip 60 before the patient begins taking the medication 15. Although the memory strip 60 is shown and described as being secured to a paper backing 51, it should be understood that the memory strip 60 could be affixed directly to the inner or outer surface 26 or 27 of the vial 20 or even imbedded in the vial. While the memory device 60 is described and shown as having the shape of a strip, it should be understood that differently shaped memory devices could be used without departing from the invention.

Figure 8:
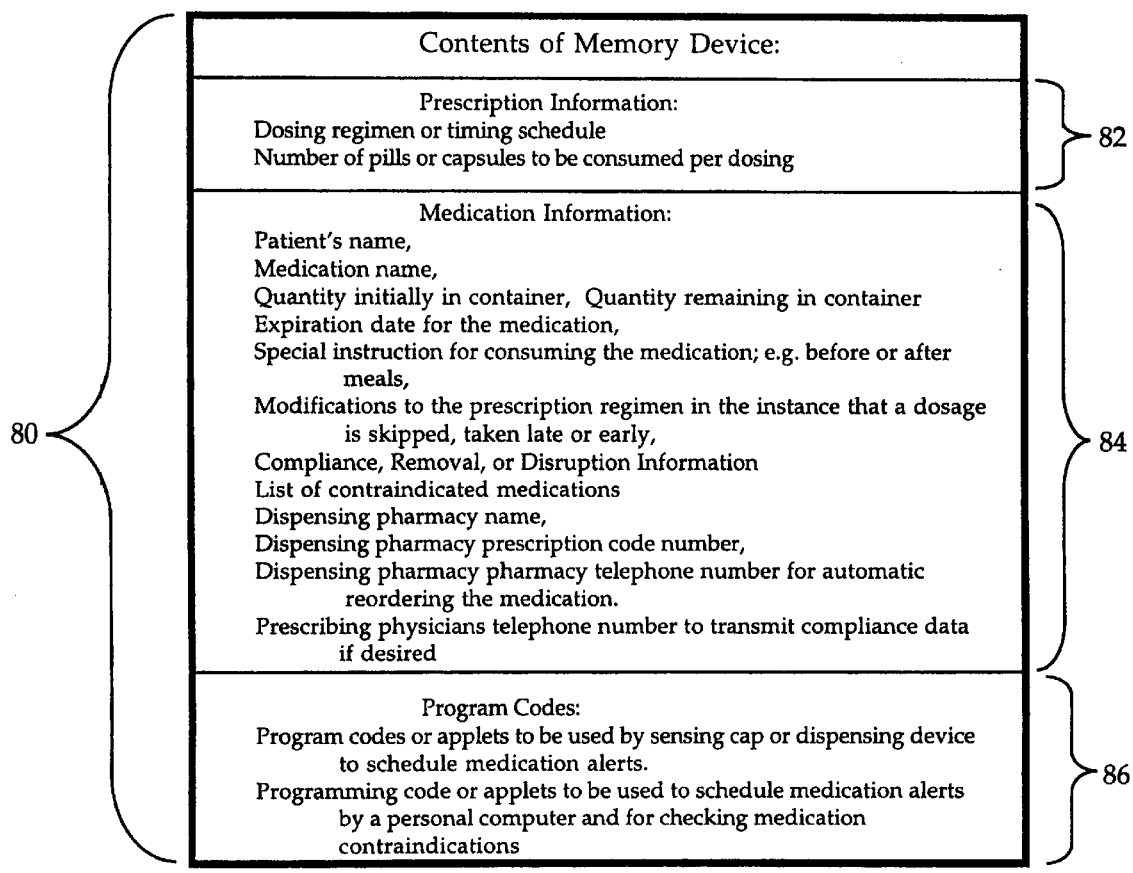
FIG. 8 is a chart listing a variety of prescription information and program codes that can be contained in the memory strip of the interactive label.

As shown in FIG. 8, the memory strip 60 contains a variety of information 80. The contents of the information 80 includes prescription information 82 such as information defining the dosing regimen and the number of pills or capsules to be consumed per dosing. The memory strip 60 also contains medication information 84 and program codes 86 for downloading into or otherwise being sensed or read by the computer processor 120 of the automated cap 100. The electrical contacts 62 and wires 64 communicate with the memory strip 60 so as to access the information 80 in or write additional information to the memory strip. As discussed below, the memory strip 60 can be electronically altered or written to via the processor 120 to store information designating when the cap 100 is removed and reattached to the vial 20, such as removal information 84 indicating that a dose of medication 15 was removed from the vial, quantity information 84 regarding the number of doses remaining in the container, or removal time, disruption or compliance information 84 indicating actual compliance to the prescribed dosing regimen 82. It should be understood that any combination of predetermined information taken from the contents 80 of the memory strip 60 could be communicated to the computer processor 120. The computer processor 120 could use the predetermined information to select or develop desired information for communicating to the patient or care giver.

Figure 7:
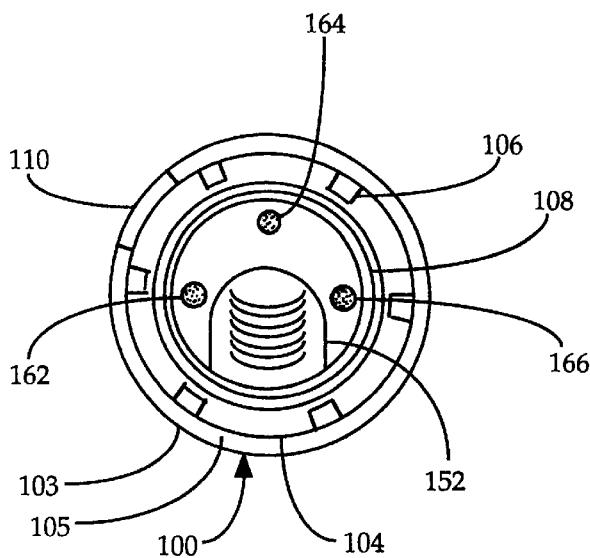
FIG. 7 is a plan view showing the underside of the automated cap used in the first vial-type embodiment of the invention.

As best shown in FIGS. 4, 5 and 7, the cap 100 includes a main body 101 with a top portion 102 and a cylindrical rim 103 having an inside surface 104 and a lower edge 105. The cap 100 includes several hold down lugs 106 and a resilient disc much like those in conventional caps of the type shown in FIG. 1. The hold down lugs 106 are located around the inside surface 104 of the rim 103 near its lower edge 105. The number of hold down lugs 106 coincides with the number of ratchets 40, and the lugs are evenly spaced to align with the ratchets. The resilient disc 108 is attached to the inside surface of the cap 100.

The ratchets 40 interact with the hold down lugs 106 to form a relatively tight, child resistant or childproof seal between the cap 100 and the vial 20. This is accomplished by placing the cap 100 over the open end 25 of the vial 20 so the lugs 106 are aligned directly between the securement ratchets 40. (See FIG. 10). The cap seals the open end 25 of the vial 20 when in this removably aligned position, but the cap is not secured to the vial. The cap 100 is then depressed and rotated clockwise so that each lug slides up the wedge 45 of its corresponding ratchet located to its left, and into a secure position where each lug rests inside the cup 42 of its corresponding ratchet 40. (See FIG. 11). When in this secured position, the resilient disc 108 biases the lugs to remain inside the cups 42 of their corresponding ratchets 40 due to a spring-like force exerted by the resilient disc 108 against the open end 25 of the vial 20. The hold down lugs 106 and ratchets 40 prevent the simple counterclockwise rotation of the cap, and thus its removal. Instead, the cap 100 must be pushed down to compresses the flexible membrane 108, releasing the contact between the lugs 106 and the ratchets 40, before the cap can be rotated counterclockwise.

Figure 6:
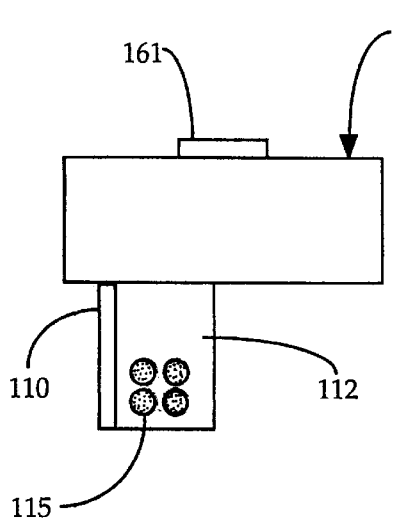
FIG. 6 is an elevation view of the automated cap showing the sensors that engage the electrical contacts of the memory strip.

The automated cap 100 includes a sensing device or sensing tab 110 for sensing the contacts 62 of the memory strip 60. The sensing tab 110 projects down from the edge 105 of the rim 103 of the cap 100. As shown in FIG. 6, the sensing tab 110 has an inside surface 112 with sensors 115. The sensors 115 are positioned to align with the contacts 62 of the memory strip 60 when the cap 100 is in the secured position on the open end 25 of the vial 20. The sensors 115 electrically engage the contacts 62. Predetermined information 80 in the memory strip 60 is electronically transmitted to or otherwise communicated or read by the computer processor 120 via the contacts 62, links 64, sensors 115 and, as discussed below, a circuit board 130.

The sensing tab 110 extends through the opening 31 in the guide ring 30. The opening 31 is sized so that the cap 100 can only be attached to the vial 20 in the one position which aligns the sensors 115 of the sensing tab 110 into electrical engagement with the contacts 62 of the memory strip 60. Specifically, the cap 100 can only be placed on the open end 25 of the vial 20 with the sensing tab 110 abutting or nearly abutting the right end 32 of the guide ring 30. The cap 100 is then rotated in a clockwise direction until the sensing tab 110 abuts or nearly abuts the left end 34 of the guide ring 30 and the hold down lugs 106 have come to rest in the cups 42 of the securement ratchets 40 so that the cap 100 is in its secured position on the vial 20.

Figure 9:
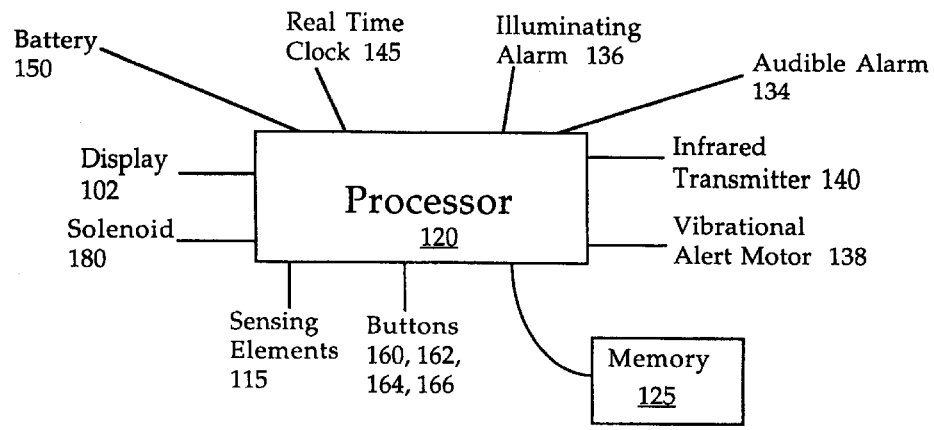
FIG. 9 is a schematic diagram showing the circuitry in the automated cap.

As shown in FIG. 9, the automated cap 100 includes a computer processor 120 having its own memory 125. The processor 120 and memory 125 are located on and in electrical communication with a circuit board 130 located inside the cap 100 for protection. (See FIG. 4.) The circuit board 130 electrically connects the processor 120 to a visual communication device such as an LCD display 132. The LCD display 132 visually displays desired information to the patient, such as the date and time the next dose of medication is to be taken and the number of pills to be taken. The display 132 can also indicate an alert or warning to the patient, such as the fact that the patient is so overdue in taking a dose of medication that that dose should no longer be taken. The circuit board 130 also electrically connects the processor 120 to a variety of alarming devices such as audible, visual and vibrational communication devices or alarms 134, 136 and 138, respectively. These alarms 134, 136 and 138 indicate a variety of warnings to a patient, such as when it is time to take a dose of medication. The circuit board 130 also electrically connects the processor 120 to a communication device such as an infrared transmitter 140 that transmits information to or receives information from a separate personal or business computer 270 as discussed below.

As shown in FIGS. 4 and 9, the circuit board 130 is in electrical communication with a battery 150 that powers the processor 120, the display 132, alarms 134, 136, and 138, transmitter 140 and a timing device such as a real time clock 145. An access panel 152 is provided to allow periodic replacement of the battery 150. The access panel 152 is prevented from accidental opening by friction between it and cap 100. In addition, when the cap 100 is secured to the vial 20, the battery access panel 152 cannot slide out due to interference between the wall 22 of the vial 20 and the access panel. Accordingly, the battery 150 should not fall into the medication 15 and accidentally consumed.

The circuit board 130 is in electrical communication with a button 160 for electromechanically communicating information to the processor 120. (See FIG. 2). By pressing button 160, the patient is able to send an electrical signal to the processor 120 in response to a question shown on the display 132 or to indicate an action to be taken, such as turn off an alert or alarm. Button 160 is surrounded by a raised ring 161 to protect it from inadvertent contact as it is located on the outside surface of the cap 100. Additional buttons 162, 164 and 166 (see FIG. 7) are located on the inside surface 104 of the cap 100 to enable the patient to set the correct date, hour and minute of the real time clock 145 that is in electrical communication with the processor 120 via the circuit board 130. The computer processor 120 uses the prescribed dosing regimen information 82 and the timing device 145 to calculate or otherwise develop the prescribed times for taking the medication 15. The timing device 145 informs the computer processor 120 when the predetermined times to take the medication occur. The computer processor then informs the patient or individual that it is time to take a dose of medication 15 via the display 132 or an alarm 134, 136 or 138. While buttons 162, 164 and 166 are located on the inside surface 104 of the cap 100, it should be understood that the buttons could be located on the outside surface of the cap as well.

Figure 10:
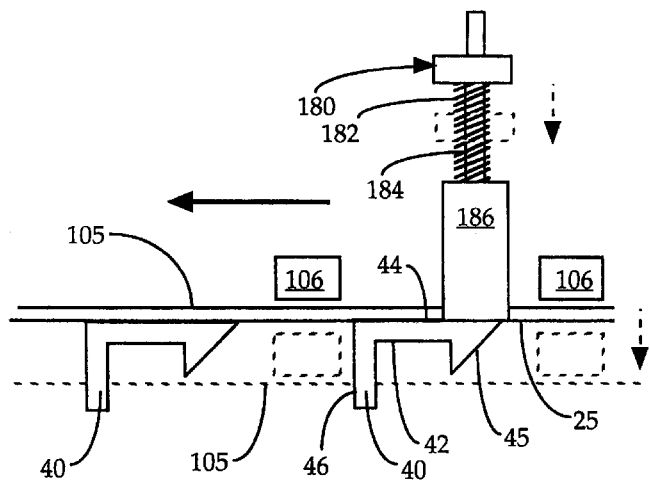
FIG. 10 is an enlarged, diagrammatic view of a portion of the automated cap positioned over the vial, the armature of the locking mechanism of the cap engaging the top of one securement ratchet of the vial, and a pair of hold down lugs of the cap aligned between the securement ratchets of the vial.
Figure 11:
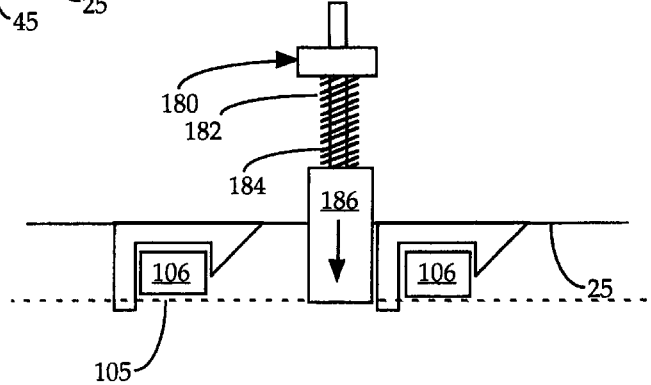
FIG. 11 is an enlarged, diagrammatic view of a portion of the automated cap in a locked position on the vial, the armature of the locking mechanism of the cap received between the securement ratchets of the vial, and the hold down lugs being received in the cup of its respective securement ratchet.
Figure 12:
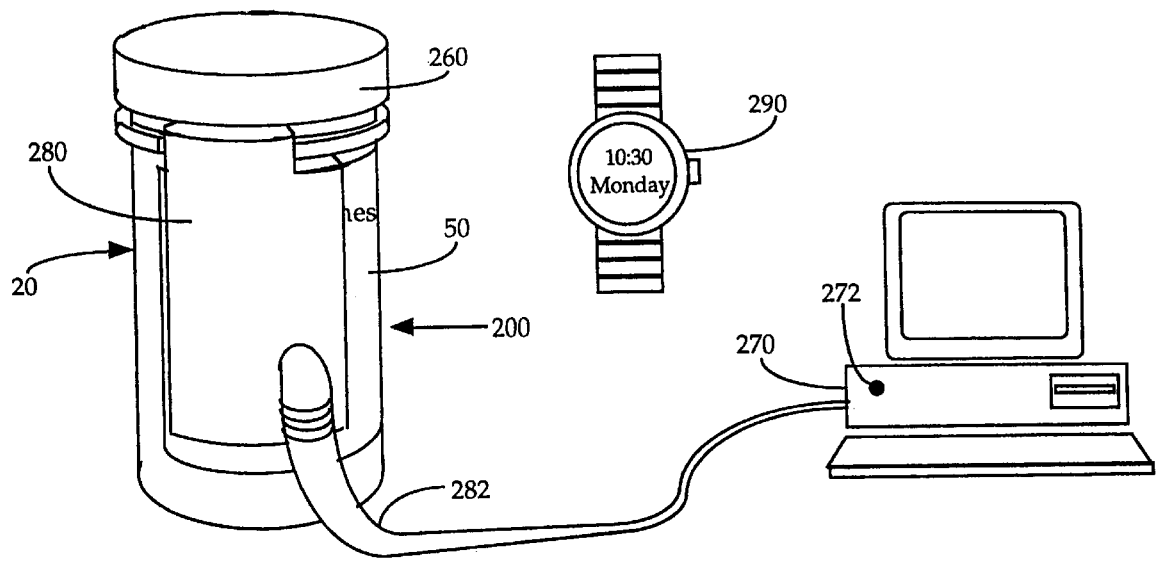
FIG. 12 is a perspective view of a second embodiment of the invention where the medication container includes a conventional, non-automated cap that seals a vial with an interactive label, and a sensing element and cable that conveys information to a separate computer or personal alerting device.
Figure 13:
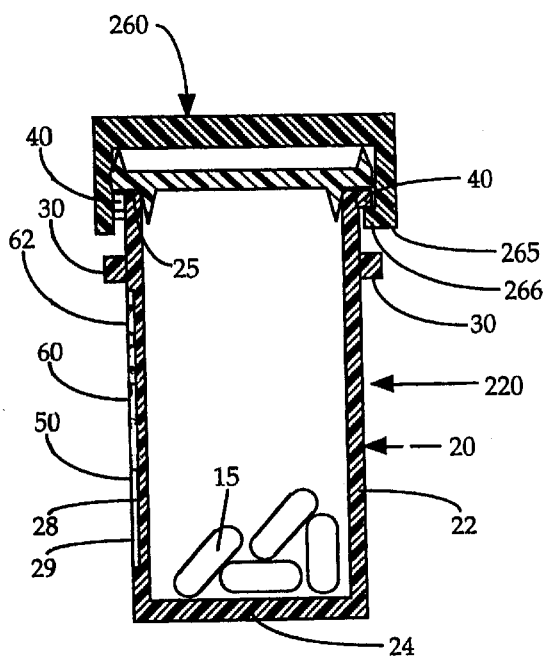
FIG. 13 is a cross-sectional view of a second embodiment of the invention where the medication container includes a cylindrical vial with an interactive label having an electronic memory strip, and a conventional cap.

As shown in FIGS. 9–11, automated cap 100 further includes an access control device formed by the computer processor 120 and a device such as solenoid locking assembly 180 that is in electrical communication with the processor via the circuit board 130. The locking assembly 180 controls the patient's ability to access and remove the medication 15 from the vial 20 until the time the next dose of medication is due according to the prescribed dosing regimen. The assembly 180 includes an armature 182 and a spring 184 for biasing a plunger 186 into a normal, extended position as shown in solid lines in FIGS. 10 and 11. As explained above, to seal the vial 20, the cap 100 is first aligned with open end 25 of the vial so that the hold down lugs 106 are positioned above and in between the ratchets 40 of the vial. (See FIG. 10). The cap 100 is then depressed into a removably aligned position over the open end 25 so that the lugs 106 move directly between the ratchets 40. The plunger 186 contacts the upper surface 44 of the ratchet 40 which causes spring 182 to compress. This is shown in FIG. 10 in phantom lines. The cap 100 is then rotated clockwise into its secured position where each hold down lug 106 rests in the cup 42 of its respective ratchet 40. When in this secured position, plunger 186 clears the side 46 of the ratchet 40 so that spring 184 biases the plunger into its normal, extended position. Attempts to remove the cap 100 by rotating it counterclockwise are resisted by plunger 186 which abuts the side 46 of the ratchet 40. The cap 100 is now locked into its secured position. The processor 120 is programmed to activate the solenoid locking assembly 180 to draw up the armature 182 and plunger 186 when the next medication dosage is due to be taken. Only then can the cap 100 be rotated counterclockwise and removed.

Operation of First Embodiment

When the automated cap 100 is secured to the medication vial 20 the sensors 115 on the tab 110 of the cap are in electrical contact with the contacts 62 of the memory strip 60, and the information 80 in the memory strip is electrically communicated to or otherwise read by the processor 120 of the cap via the contacts 62, sensors 115 and circuit board 130. Predetermined portions of information 80 from the memory strip 60 are compared with the information that had previously been read and stored in the memory 125 of the cap 100. If the predetermined information 80 is the same as before, the processor 120 will compute the next prescribed time for taking a dosage of medication 15 and activate an alarm or otherwise communicate that information to the patient when that time occurs. If the cap is not returned to seal the vial 20 to which it was previously attached, the audible alarm 134 will be activated by the computer 120. The patient or care giver can disable the alarm 134 by securing the cap 100 back on the correct vial 20. If the cap 100 is not returned to the correct vial 20 and the alarm 134 is ignored for a period of time or the user presses button 160, the alarm is disabled, and the new information 80 in the new memory strip 60 is stored in the memory 125 of the cap 100 and used to compute the next dosage time for the new medication. The automated cap 100 will keep an accurate count of the number of times the medication container is opened each day and advise the patient against consuming too many pills in too short a time. This is particularly useful for medications 15 that are prescribed to be used on an as needed basis (e.g. pain medication), but not to be consumed more than a certain amount in any given day.

When the automated cap 100 is removed, it can no longer read the memory strip 60. This triggers an event that can be used to store the current date and time in memory 125 of the cap 100. When the cap 100 is resecured to the vial 20, the date and time are written to memory 125 or to the memory strip 60 indicating that the patient took a dose of medication 15 and the actual consumption time. The times and dates stored reflect consumption compliance information or compliance data in adhering to the prescription regimen. The actual compliance data 84 can be conveyed to a separate personal or business computer 270 via an interface in the computer (not shown) that can sense a controlled flashing of the illuminating alarm 136. By pressing button 160 for a period of several seconds the automated cap 100 will transmit the compliance data 84. The compliance data 84 may also be conveyed via the infrared transmitter 140 in the automated cap 100 to an infrared receiver 272 in the computer 270. The compliance data 84 is used by the physician to determining if the patient is taking too much or not enough medication 15, or is not adhering to the regular timing specified by the prescription.

By comparing the quantity of medication 15 in the container 10, as stored as medication information 84 in the memory strip 60, against the number of times the automated cap 100 was removed and the number of pills to be consumed in each dosage, the automated cap 100 can compute the inventory of medication in the container 10, when the prescription should be refilled and alert the patient. The number of times the container 10 is opened and the numbers of doses consumed is written to the memory 125 of the cap 100 or the memory strip 60 of the interactive label 50.

As stated above, the information 80 contained in the memory strip 60 can be transmitted to a separate personal or business computer 270 or personal alerting device 290, such as a digital watch or appointment book, by equipping the automated cap 100 with an infrared transmitter 140. The transmission is started by pressing button 160 for several seconds. The transferred information is used to establish an alert timing schedule 82 to remind the patient when to take the medication 15. This is accomplished by having the computer 270 activate a variety of its alarms, or by having the computer page the patient with a message to consume a specific medication, or by calling the patient using a telephone to convey a verbal message to consume a specific medication. In this manner, the patient can extend the alarm and alerting devices beyond what is available in the cap 100, or to have alerts be issued even if a conventional cap is used.

If a patient is taking several medications 15 and the information 80 contained in the memory strip 60 for each container 10 is transferred to a separate personal or business computer 270, the computer can reference and compare the lists of contraindicated medications which are part of the medication information 84. Should two or more medications 15 be contraindicated for use together, the patient will be alerted to this fact. Every time a medication 15 is issued to a patient, the most recent list of contraindications is included in the memory strip 60 of the container 10. If the patient does not have a software program capable of performing this function, the program codes 86 will contain a program that is transferred from the memory strip 60 to the computer 270 to perform this check. This program may use a Java programming language so that it can be used in a wide variety of computer processors 270. Other program codes 86 can be sent to the automated cap 100 or computer 270 to perform various alerting functions.

Second Embodiment

FIGS. 12–15 show a second embodiment of the invention where the container 200 includes a conventional, childproof cap 260 as shown in FIG. 1, in place of the automated cap 100. The vial and interactive label that are interchangeable with the vial 20 and label 50 of the first embodiment. The interactive label 50 is electrically linked to the separate personal or business computer 270 via a sensing element 280. The conventional cap 260 is secured to the vial 20 via securement ratchets 40 as in the first embodiment. The guide ring 30 is located a predetermined distance from the top end 25 of the vial 20 so that the ring does not interfere with securing the conventional cap 260 to the vial 20.

The information 80 contained in the memory strip 60 is electronically conveyed to computer 270 by sensing element 280. Sensing element 280 has sensors 281 located on its inside surface in a pattern and position similar to the contacts 62 of the memory strip 60. The sensing element 280 has an arcuate shape to matingly engage the cylindrical wall 22 of the vial 20 so that when the sensing element is aligned with and placed over the interactive label 50 its sensors 281 are in electrical contact with the contacts 62 of the memory strip 60. The sensing element 280 includes a connecting cable 282 with an electronic connector 284 adapted to be plugged into or otherwise electrically communicate with the computer 270. Sensing element 280 has an upper tab sized to fit snugly into the opening 31 between the ends 32 and 34 of the guide ring 30. This can be accomplished when the conventional cap 260 is in place as shown in FIG. 11. It should also be understood that the sensing element 280 can be used to transfer predetermined information 80 to or from the memory strip 60 of either the first or second embodiment of the container 10 or 200 to the computer 270. When the sensing element 280 is used with the first embodiment, the automated cap 100 must be removed.

Third Embodiment

FIGS. 16 and 17 show a third embodiment of the invention where the container 300 includes a modified interactive label 350 and an automated cap 370 with a modified sensing tab 372. Cap 370 is otherwise interchangeable with cap 100. The container 300 includes a vial that is interchangeable with the vial 20 in the first embodiment. The label 350 includes two rows of conductive or non-conductive contacts 352 and 354. These contacts 352 and 354 can also take the form of reflective or non-reflective surfaces. These contacts or surfaces 352 and 354 represent 1s and 0s. The contacts or surfaces 352 and 354 combine to form a code representing the prescription regimen.

The inside surface of downwardly projecting sensing tab 372 includes sensors 374 that detect the presence or absence of a conductive or reflective surface 352. When the surfaces are conductive, one of the conductive surfaces 352 acts as a ground surface 356 for the remaining surfaces 352. By detecting a voltage or current between the ground 356 and any of the other conductive surfaces 352 a bit of information may be read as a 1 or a 0. By combining the bits of information together, a binary number may be created that can represent a prescription information 202.

In FIG. 16, there are a total of ten contacts or surfaces 352 and 354. One contact or surface is the ground 356. Another second contact or surface 358 is used to sense when the cap 370 is removed. Of the eight remaining contacts or surfaces 352 and 354, two are used to indicate the dosage, for example a 0 may represent one pill, a 1 to indicate two pills and a 2 to represent three pills, and a 3 to indicate four pills are to be taken as each dosage. The remaining six contacts or surfaces are combined to represent a number between 0 and 63. These surfaces 352 and 354 are used to represent the timing of the prescription regimen, 0 to represent a dosage every 2 hours, a 1 to indicate a dosage every 3 hours, a 2 to indicate a dosage every 4 hours and so on. While ten surfaces are shown and described, it should be understood that more or fewer may be used.

The conductive or reflective surfaces 352 may be part of a larger conductive or reflective surface (not shown). A non-conductive or non-reflective surface 344 may be created by punching a hole in or printing over a portion of the larger conductive or reflective surface. This process may be done as the label 350 is printed with the readable text 44.

The automated cap 370 is secured to the vial 20 the same way as in the first embodiment. The cap 370 includes the same processor 120, memory 125, circuit board 130, display 132, alarms 134–138, transmitter 140, clock 145, battery 150 and buttons 160–166 as automated cap 100. When the cap 370 is removed from the vial 20, the conductive path between ground surface 356 and second surfaces 358 is broken indicating to the cap 370 that a dosage of the medication is being taken. The braking of this conductive path is also used to set the alarms to indicate when the next dosage should be taken.

Fourth Embodiment

FIGS. 18–24 show a fourth embodiment of the invention where the container 400 is a single dosage, disk shaped, blister pack and an interactive label 450 with a memory strip 460. The blister pack 400 is placed in a dispenser 500 having a computer processor 530 that controls a display and a variety of alarms. Memory strip 460 is functionally and structurally substantially interchangeable with memory strip 60. It should be understood that in this embodiment of the invention, the dispenser 500 forms a part or piece of the container 400.

Figure 18:
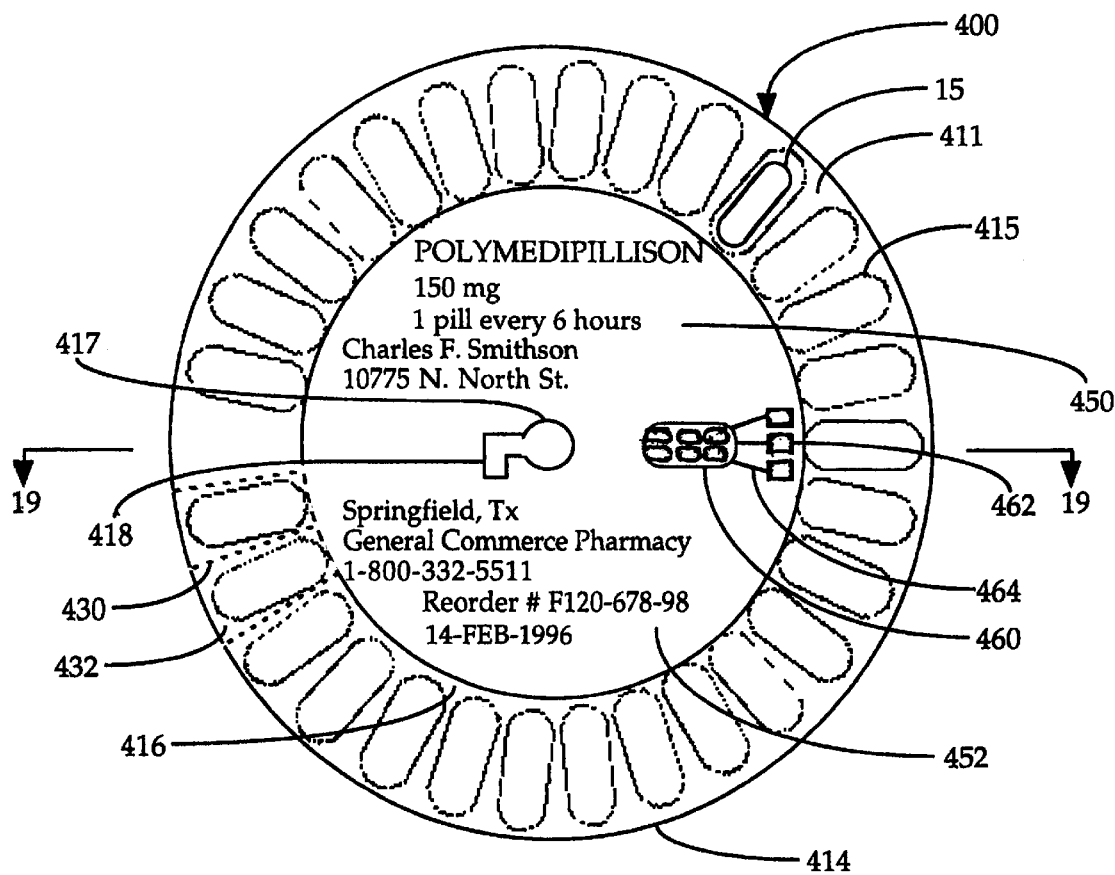
FIG. 18 is a top, plan view of a fourth embodiment of the present invention where the medication container is a disc shaped blister pack with an interactive label having an electronic memory strip affixed to a central surface of the blister pack.
Figure 19:
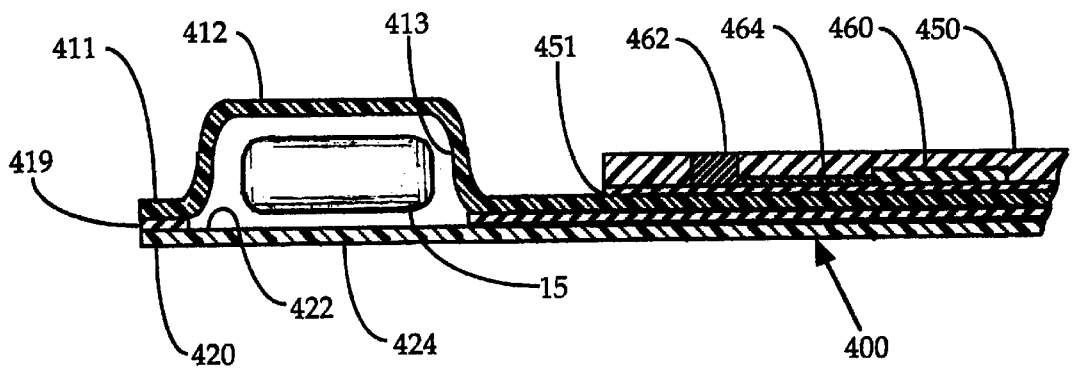
FIG. 19 is a side, cross sectional view of FIG. 18 taken along line 19—19 showing a dose of medication in a pocket of the blister back and the interactive label affixed to the tear resistant sheet.
Figure 20:
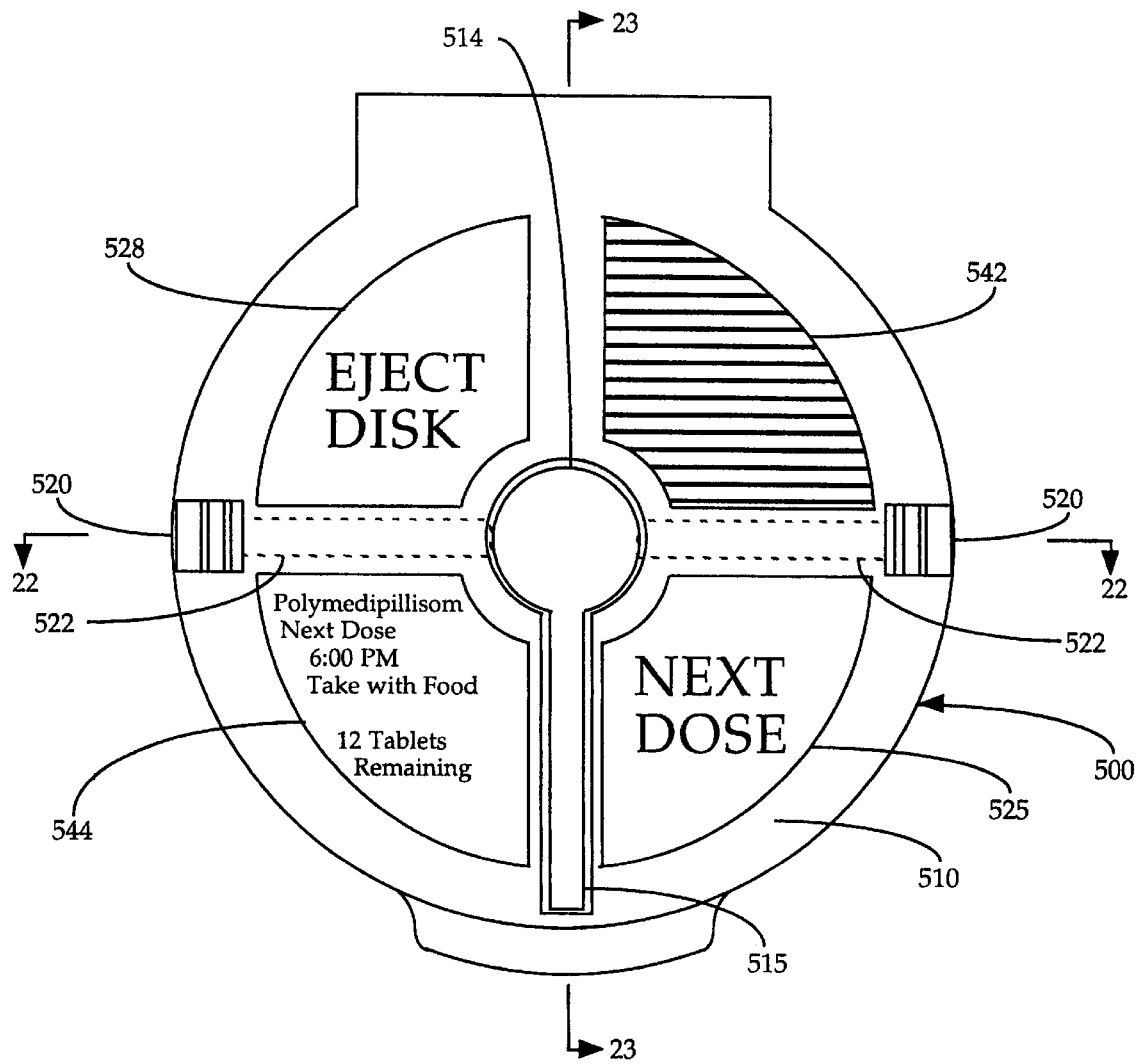
FIG. 20 is a top, plan view showing the lid of a semi-automated dispenser equipped with a dispensing lever, finger latches, a display, an audible alert, "Eject" and "Next Dose" buttons.
Figure 21:
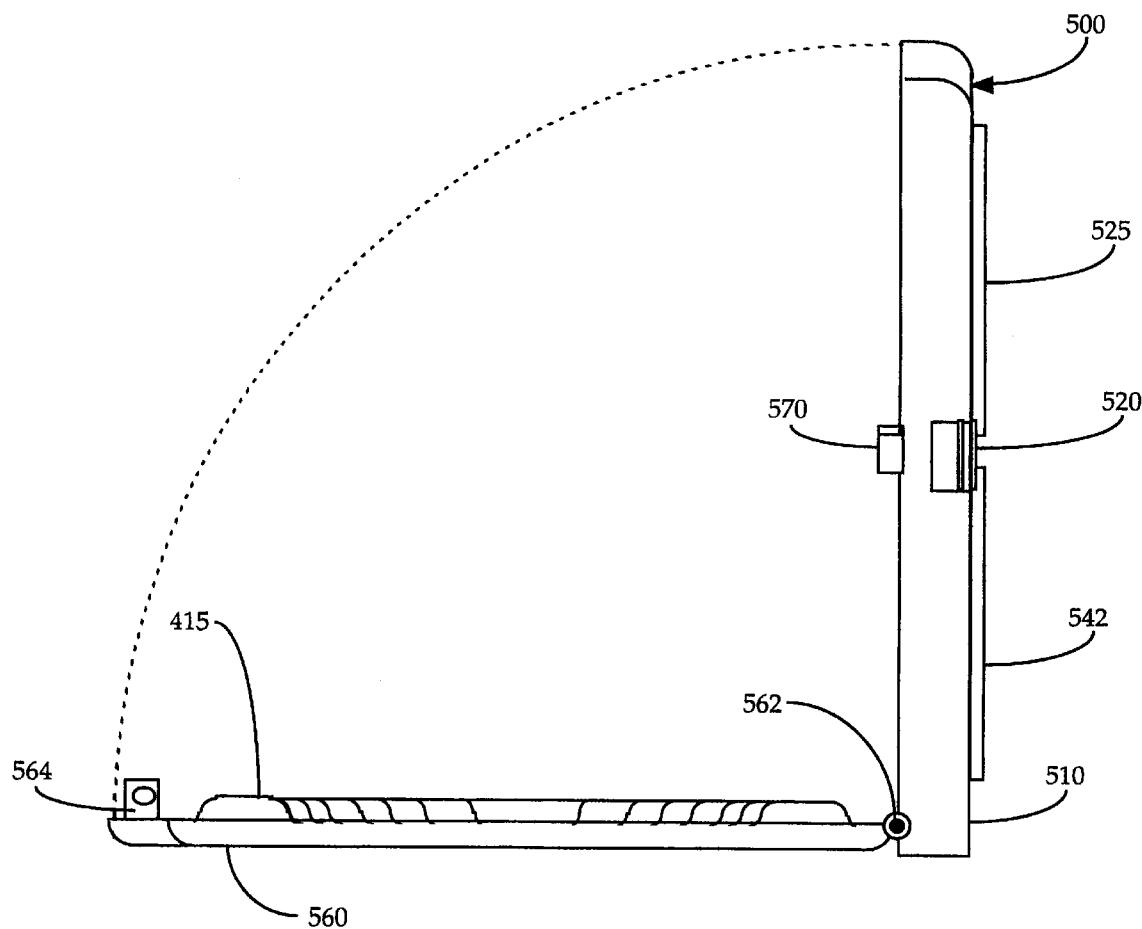
FIG. 21 is a side, plane view showing the disc shaped blister pack inside a semi-automated dispenser in an opened position.
Figure 22:
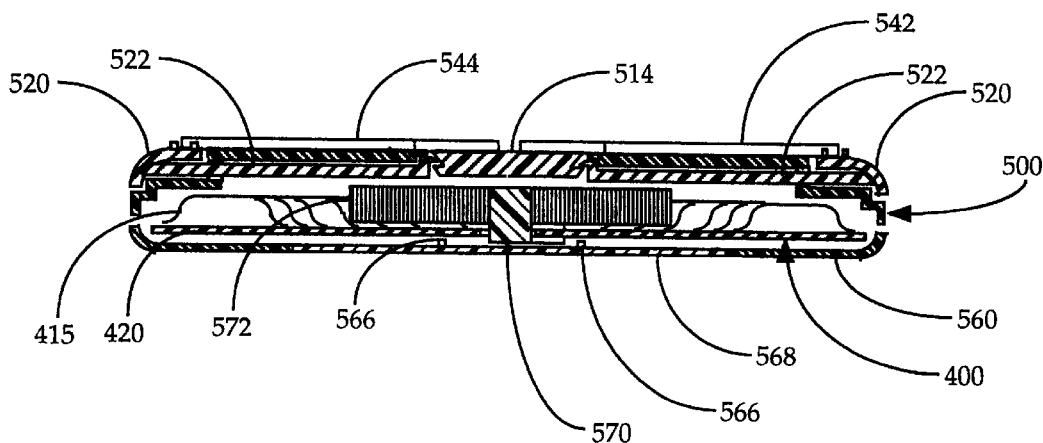
FIG. 22 is a side, cross-sectional view of FIG. 20 taken along lines 22—22 and showing the semi-automated dispenser with its plunger in a locked position.

FIGS. 18 and 19 show a blister pack 400 formed by a tear resistant sheet 411 having front and rear surfaces 412 and 413 and a perimeter 414. The tear resistant sheet 411 is formed into multiple pockets 415 located around its perimeter 414. Each pocket 415 holds a single dose of medication 15. The tear resistant sheet 411 has a substantially flat central area 416 with a central opening 417 and offset notch 418 formed through the sheet 411. The rear surface 413 of the tear resistant sheet 411 has an adhesive coating 419 applied to it, except in pockets 415. The blister pack also includes a backing sheet 420 having front and rear surfaces 422 and 424. The front surface 422 is secured to the rear surface 413 of the tear resistant sheet 411 via the adhesive coating 419. The backing sheet 420 extends over the pockets 415 so that each doses of medication 15 is sealed into its respective pocket. The tear resistant sheet 411 has perforations 430 that separate each pocket 415 into a discrete portion 432 that is separable from the remainder of the container.

An interactive label 450 is attached to the flat, central area 416 of the front surface 412 of the tear resistant sheet 411 via an adhesive layer 451. The label 450 has a textual portion 452 with prescription information printed on its front surface. The label 450 includes a memory strip 460 similar to that used in the first and second embodiments. The information in the memory strip 460 is the same as the information 80 in the first and second embodiments. The electronic memory strip 460 is sensed through its contacts 462 via an electrical connection or wire 464. The opening 417 and notch 418 in blister pack 400 are used to mount the single dosage container 400 into a predetermined position in the dispensing device 500. The opening 417 and notch 418 ensure that the blister pack 400 is placed in a secure position in said dispenser 500, and that the sensing contacts 462 are aligned with sensors for electrically communicating with the memory strip 460.

Figure 23:
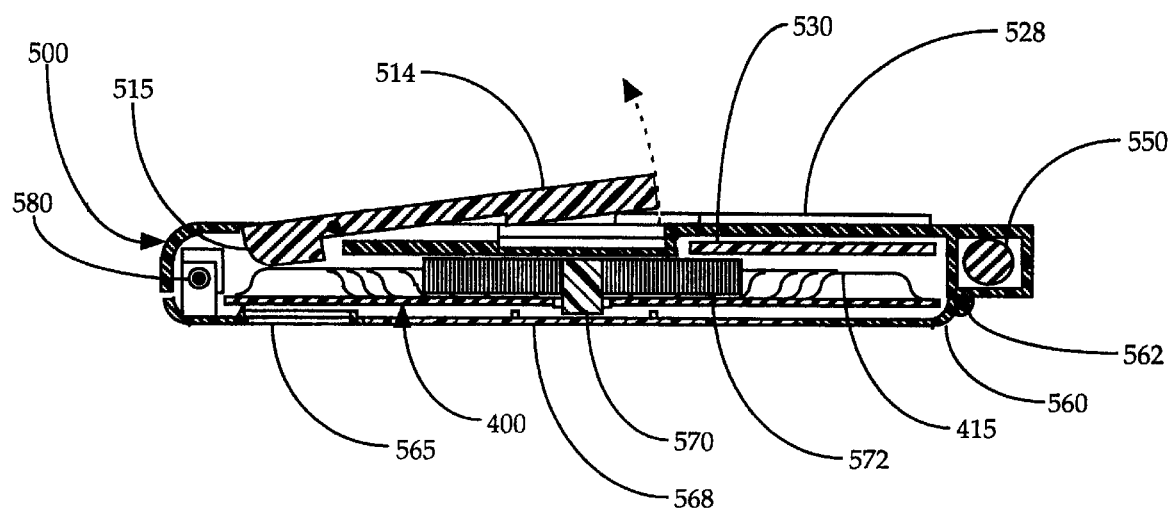
FIG. 23 is a side, cross-sectional view of FIG. 20 taken along lines 23—23 and showing the semi-automated dispenser with its plunger being raised into a dispensing position.

FIGS. 20–23 show the semi-automated, clam shell medication dispenser 500 for housing and dispensing medication 15 from the blister pack container 400. The dispenser 500 has a lid 510 with a dispensing lever 514 and a plunger 515 that combine to form a dispensing mechanism for dislodging a dose of medication 15 from its pocket 415 in the blister pack 400. Finger latches 520 are arranged on both sides of the dispensing lever 514 and plunger 515. The latches 520 are integrally connected to locking struts 522 which engage the dispensing lever 514. (See FIG. 20). To dispense a dose of medication 15, the patient pushes each finger latch 520 out and away from the body of the lid 510 so that struts 522 release the dispensing lever 514. When released, dispensing lever 514 is biased by a spring (not shown) to a raised position above the struts 522 as seen in FIG. 23. When the finger latches 520 are released, the latches and struts 522 are biased by a second spring (not shown) into their original position. The struts 522 are now located beneath the dispensing lever 514. This structure is intended to provide a relatively child-proof or resistant method for releasing dispenser lever 514.

The dispenser 500 is now ready to dispense medication 15. The lever 514 is pulled up, which causes dispensing plunger 515 to rotate down and press against the top of the blister pack pocket 415 positioned below the plunger. As the plunger continues to rotate down, the medication 15 is forced through backing sheet 420 of the single dose container 400 and through a dispenser opening 565 for the patient to consume. The predetermined information 80 in the memory strip 460 is downloaded to or sensed by the processor 530 of the dispenser 500 via a sensing mechanism (not shown) attached to the lid 510. The sensing mechanism has sensors similar to those in sensing tab 110. These sensors engage the contacts 462 of the memory strip 460. The computer processor 530 has circuitry similar to that shown in FIG. 9 and includes a memory and a real time clock that are electrically connected via a circuit board. Information 80 in the memory strip 460 is electronically transmitted to or otherwise communicated or read by the computer processor 530 via the contacts 462, links 464, sensors and the circuit board. The lid 510 also includes a "Next Dose" button 525 for advancing the single dosage container 400 to the next dosage position, and an "Eject" button 528 for ejecting the container 400. Communication devices such as audible alerting device 542 and display 544 are used to present messages and visual alerts. These buttons 525 and 528 and communication devices 542 and 544 are in electrical communication with the computer processor 530 via the circuit board.

Figure 24:
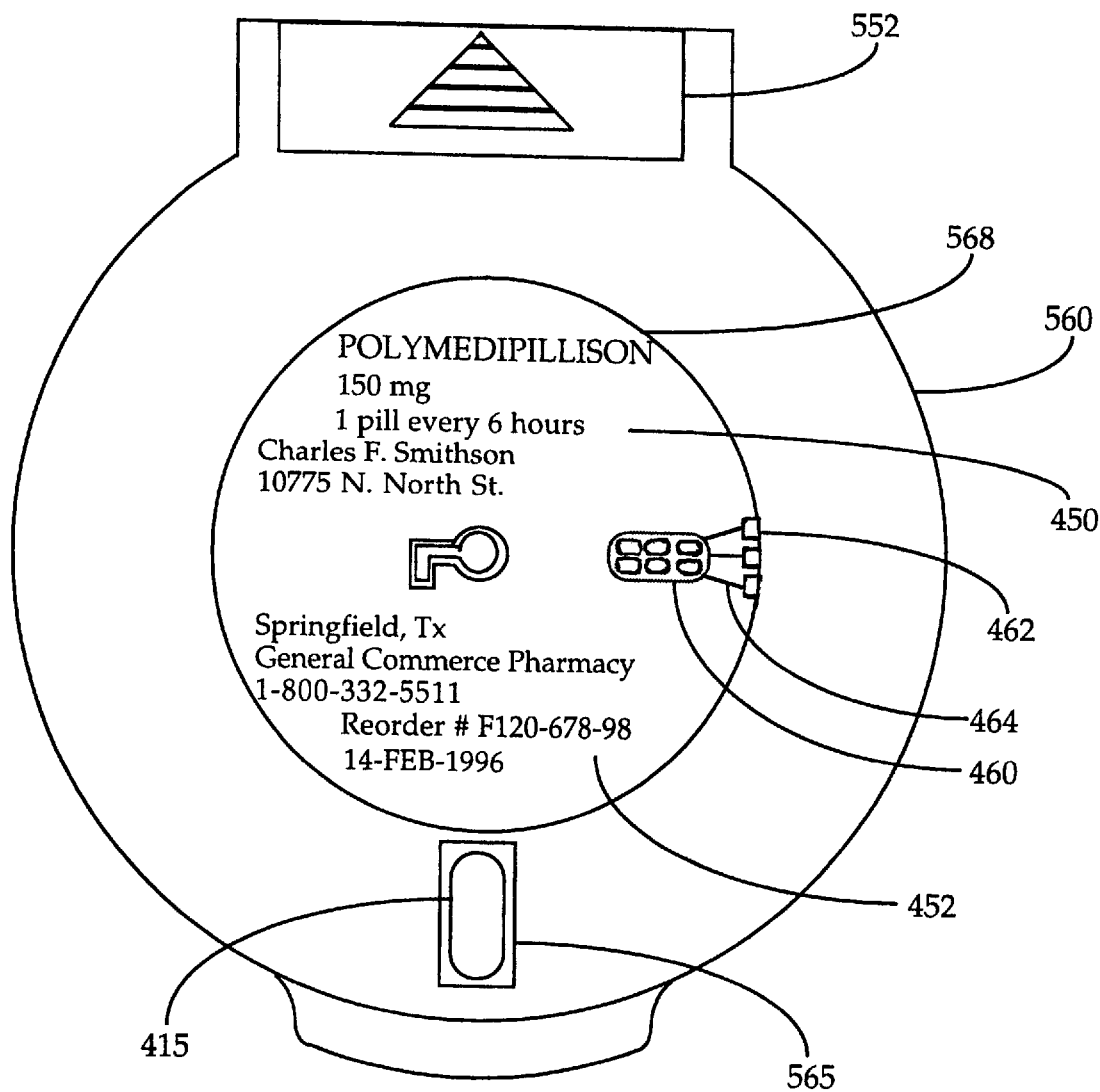
FIG. 24 is a bottom, plan view of the dispenser showing an alternate embodiment of the blister pack container where the interactive label is secured to the backing sheet of the blister pack so that the textual portion of the label is visible through a window in the base of the dispenser.

The dispenser 500 has a base 560 that is hingably attached to the lid 510 by hinge 562. The base 560 includes a battery 550 for powering the electrical components in the dispenser, and a battery access door 552 to permit periodic replacement of the battery. The base 560 has a dispenser opening 565 through which the backing sheet 420 of one of the discrete portions 432 of the blister pack 400 can be seen, and through which individual doses of medication 15 are dispensed. To assist in breaking or tearing the backing sheet 408, a portion of the dispenser opening 565 has a sharp interior edge that cuts into the surface of the backing sheet 420 as the sheet is pressed against the edge. The base 560 of the dispenser 500 also includes a flange 564 that secures the lid 510 to the base 560 when in the closed position. Alignment ribs 566 project upwardly from the inside surface of the base 560 to keep single dosage container 400 adequately raised so a drive spindle 570 passes through the central opening 417 in the tear resistant sheet 411 when the dispenser 500 is closed. The alignment ribs 566 and the shape of the spindle 570, which matingly engages the central opening 417 and offset notch 418 of the blister pack 400, combine to form a mechanism for selectively aligning one of the pockets 415 with the plunger 515 of the dispenser. FIG. 24 shows an alternate embodiment of the blister pack container 400. In this embodiment, the interactive label 450 is affixed to the surface of the backing sheet 420. A window 568 made of clear plastic is provided in the base 560 of the dispenser 500. The window 568 allows the patient to read the contents of the prescription text 452 when the dispenser is closed.

The dispenser 500 is equipped with a drive spindle 570 and a motor 572 for automatically dispensing the medication 15. The motor 572 is relatively flat in design similar to those used in portable CD players. The computer processor 530, motor 572 and spindle 570 combine to form an access control device or advancing mechanism for rotating the single dosage container 400 when a dose is to be dispensed. The computer processor 530 controls the activation of the motor 572 and spindle 570 to prevent the patient or care giver from removing medication 15 from the blister pack 400 until the time the next dose of medication is due. The motor 572 also controls a locking solenoid 580 that prevents inappropriate access to the medication container 400 by the patient or care giver. The solenoid 580 controls a rod aligned to selectively engage or enter an opening in flange 564. When the solenoid 580 is activated to force the rod into the latch opening, the dispenser 500 is locked shut. When the solenoid 580 is activated to pull the rod out of the latch opening the dispenser 500 can be opened.

Operation of Fourth Embodiment and Dispenser

To use the personal semi-automated medication dispenser 500, the patient can press the "Eject" button 528 and insert a full blister pack container 400. Processor 530 causes the single dosage container 400 to rotate via motor 472 such that the contacts 462 of the memory strip 460 are below the sensors of the dispenser 500 (not shown) which are in electrical communication with the computer processor 530 via the circuit board. When properly positioned the processor 530 may write to the memory strip 460 to update it with the number of doses that have been dispensed, so the quantity of medication 15 stored in memory strip 460 is accurate. When all the medication 15 is dispensed, the computer processor 530 is programmed to accept input from the "Eject" button 528. The computer processor 530 then causes locking solenoid 580 to retract and allow hinged lid 510 to open under spring force. The existing single dosage container 400 is removed and a new one placed so that center opening 417 is pressed over drive spindle 570. The hinged top 550 is closed, causing the locking solenoid 580 to engage the opening in flange 564 and locking the dispenser closed.

The information 80 in the memory strip 460 is transferred to processor 530 so that the prescription regimen is shown on the display 544. When it is time to take a medication 15, the processor causes audible alarm 542 to sound an alert. The patient then presses the "Next Dose" button 525. Processor 530 causes motor 572 to rotate the spindle 570 and single dosage container 400 to the next available filled pocket 415. The patient then releases the dispensing lever 514, as previously described, and lifts the lever up to dispense a dose of medication 15. When this is done a micro switch or sensor (not shown) detects the dispensing of a dose of medication 15 and reduces the quantity of medication understood by the processor 530 to be held in container 400 by one. The dispensing lever 514 is then secured into its lowered position. It should be noted that the dispensing lever 514 could be adapted to engage the blister pack 400 near perforations 430 to separate an entire discrete portion 432 from the remainder of the blister pack while leaving the medication 15 inside its discrete portion. The discrete portion 432 of the blister pack 400 would then be discharged through opening 565 in the dispenser 500 so that the patient could remove the medication from the discrete portion themselves.

As previously described portions of the information 80 in the memory strip 460 can be transferred to the separate computer 270 or personal alerting device 290. Program codes 86 can be transferred so computer 270 is equipped with software to provide alert scheduling or to check for contra-indicated medications. Program codes 86 can be transferred to processor 530 of dispenser 500 to assist in scheduling alerts. Additional buttons (not shown) are used to enter the date and time. The dispenser can also be provided with other alarms (not shown) such as a visual or vibrational alarm, an infrared transmitter (not shown) for communicating with a separate computer, and connectors (not shown) for electrically attaching the dispenser to the separate computer 270.

It should also be understood that the invention as a whole may be embodied in other specific forms without departing from the spirit or central characteristics thereof. The present examples and embodiments thereof are to be considered in all aspects as illustrative and not restrictive, and the invention is not to be limited to the details given herein. It will be understood by those of skill in the art that various changes may be made and equivalents may be substituted without departing from the broader aspects of the invention. Specifically, while the invention has been shown and described as including a vial or blister pack container, it should be understood that other forms of containers could be used with equal effectiveness. For example, the container could be a tray or a cassette that does not include a cap or cover. It should therefore be understood that the container can take on a variety of shapes and forms without departing from the broad aspects of the invention.

I claim:

1. A medication container for containing doses of medication, said medication container comprising:

a first piece having inside and outside surfaces, said inside surface defining a compartment, and said compartment containing the medication;

a machine readable and writable, memory strip containing prescribed dosing regimen information for the medication, said memory strip being secured to said first piece in a predetermined location;

a second piece adapted for removable securement to said first piece, said second piece having a sensor positioned to communicate with said memory strip when said second piece is secured to said first piece, said second piece having a computer processor, a timing device and a communication device, said timing device, communication device and sensor being in electrical communication with said computer processor, said prescribed dosing regimen information in said memory strip being transmitted to said computer processor when said first piece is secured to said second piece, said computer processor using said prescribed dosing regimen information and said timing device to develop a predetermined time to take the medication, and said computer processor communicating said predetermined time to said communication device; and wherein movement of said second piece causes a disruption in said communication to said computer processor, said timing device obtaining disruption time information corresponding to said movement of said second piece, and said disruption time information being recorded in said memory strip.

2. The medication container of claim 1, and further including an access control device adapted to prevent removal of the medication from said compartment of said first piece until said predetermined time occurs.

3. The medication container of claim 2, and wherein said first piece is a vial having an open end, and said second piece is a cap adapted to be removably secured to and seal said open end.

4. The medication container of claim 3, and wherein said cap includes a plurality of hold down lugs, and said open end of said vial includes a plurality of ratchets adapted to securely engage said hold down lugs to secure said cap and seal the medication in said compartment.

5. The medication container of claim 4, and wherein said access control device is a locking mechanism located in said cap, and said locking mechanism prevents removal of said cap from said vial until said predetermined time occurs.

6. The medication container of claim 3, and wherein said vial includes a guide ring having an opening aligned with said memory strip, and said cap includes a sensing tab, said guide ring and sensing tab cooperating to facilitate communicative alignment of said sensor with said memory strip.

7. The medication container of claim 3, and wherein said memory strip contains a program for determining said predetermined time information, said program being communicated to said computer processor when said memory strip is aligned with said sensor, said program enabling said access control device to permit access to the mediation at said predetermined time.

8. The medication container of claim 4, and wherein said open end of said vial is adapted to permit securement of a standard, childproof cap to seal said open end.

9. The medication container of claim 2, and wherein said machine readable and writable memory strip is electronic, said memory strip includes a contact for accessing said information in said memory strip, and said contact is aligned in electrical communication with said sensor.

10. The medication container of claim 2, and wherein said first piece is a blister pack and said compartment is a plurality of pockets, each of said pockets containing one of the doses of medication, and said second piece is a dispenser that houses said blister pack.

11. The medication container of claim 10, and wherein said dispenser includes an aligning mechanism adapted to align one of said pockets with a dispensing mechanism that dislodges the medication through an opening in said dispenser, and said dispenser further includes an advancing mechanism for advancing said blister pack from said one of said pockets to another of said pockets.

12. The medication container of claim 10, and wherein said dispenser includes an access control device that prevents rotation of said blister pack in said dispenser until said predetermined time occurs.

13. The medication container of claim 10, and wherein said dispenser includes a second sensor for sensing when one of the medication is dispensed from said dispenser, and said time of said dispensing of the medication is recorded in said memory strip.

14. The medication container of claim 10, and wherein said memory strip contains a program for determining said predetermined time information, said program being communicated to the processor when said memory strip is aligned with said sensor, said program enabling said container to dispense one of the doses of medication at said predetermined time.

15. The medication container of claim 1, and wherein said memory strip contains prescription information, and said cap includes means for communicating said prescription information to a separate computer.

16. A medication container for containing doses of medication, said medication container comprising:

a first piece having inside and outside surfaces, said inside surface defining a compartment, and said compartment containing the medication;

a machine readable and writable memory strip containing quantity information regarding the quantity of the doses of medication in said first piece, said memory strip being secured to said first piece in a predetermined location; and, a second piece adapted for removable securement to said first piece, said second piece having a sensor positioned to communicate with said memory strip when said second piece is secured to said first piece, said second piece having a computer processor, said sensor being in electrical communication with said computer processor, and said information in said memory strip being transmitted to said computer processor when said first piece is secured to said second piece, and said sensor senses removal information corresponding to a removal of the medication from said first piece, said sensor communicating said removal information to said computer processor, and said computer processor altering said quantity information in said memory strip to indicate that said quantity of medication in said first piece has been reduced.

17. The medication container of claim 16, and wherein said first piece is a vial having an open end, and said second piece is a cap adapted to be removably secured to and seal said open end.

18. The medication container of claim 17, and wherein said cap includes a timing device in electrical communication with said computer processor, and said timing device communicates removal time information to said computer processor corresponding to said removal time information, and said computer processor communicates said removal time information to said memory strip.

19. The medication container of claim 17, and wherein said cap includes a plurality of hold down lugs, and said open end of said vial includes a plurality of ratchets adapted to securely engage said hold down lugs to secure said cap to said vial and seal the medication in the compartment.

20. The medication container of claim 17, and wherein said memory strip includes prescribed dosing regimen information, and said computer processor uses said prescribed dosing regimen information and a timing device to develop a predetermined time to take the medication, and said computer processor communicates said predetermined time to said communication device.

21. The medication container of claim 20, and wherein said cap includes an access control device that prevents removal of said cap from said vial until said predetermined time occurs.

22. The medication container of claim 20, and wherein said memory strip contains a program for developing said predetermined time, said program being communicated to said computer processor when said electronic memory strip is aligned with said sensor of said sensor.

23. The medication container of claim 19, and wherein said vial includes a guide ring having an opening aligned with said memory strip, and said cap includes a sensing tab, and said guide ring and sensing tab cooperate to facilitating communicative alignment of said sensor with said memory strip.

24. The medication container of claim 19, and wherein said open end of said vial is adapted to permit securement of a standard, childproof cap to seal said open end.

25. The medication container of claim 16, and wherein said machine readable and writable memory strip is electronic, said memory strip includes a contact for accessing said information in said memory strip, and said contact is aligned in electrical communication with said sensor.

26. The medication container of claim 16, and wherein said first piece is a blister pack and said compartment is a plurality of pockets in said blister pack, each pocket containing one of the doses of medication, and said second piece is a dispenser that houses said blister pack.

27. The medication container of claim 26, and wherein said dispenser includes an aligning mechanism adapted to align one of said pockets with a dispensing mechanism that dispenses the medication from said one of said pockets and through an opening in said dispenser, and said dispenser further includes an advancing mechanism for advancing said blister pack from said one of said pockets to another of said pockets.

28. The medication container of claim 26, and wherein said dispenser includes a separate sensor for sensing said removal information, and said separate sensor senses when the medication passes through an opening in said dispenser.

29. The medication container of claim 27, and wherein said dispenser includes a timing device and a communication device in electrical communication with said computer processor, and said memory strip includes prescribed dosing regimen information, and said computer processor uses said prescribed dosing regimen information and said timing device to develop a predetermined time to take the medication, and said computer processor communicates said predetermined time to said communication device.

30. The medication container of claim 29, and wherein said dispenser includes an access control device that prevents advancement of said blister pack in said dispenser until said predetermined time has occurred.

31. The medication container of claim 30, and wherein said computer processor obtains removal time information from said timing device corresponding to said removal information, said computer processor communicating said removal time information to said memory strip.

32. The medication container of claim 30, and wherein said memory strip contains a program for developing said predetermined time, said program being communicated to said computer processor when said memory strip is in communication with said sensor, said program enabling said access control device to dispense the medication at said predetermined time.

33. The medication container of claim 16, and wherein said memory strip contains prescription information, and said cap further includes means for communicating said prescription information to a separate computer.

34. A medication container for containing doses of medication comprising:

a vial having a wall with an outer surface and an open end;

a machine readable and writable, electronic memory strip containing predetermined information, said strip having an electrical contact for electrically accessing said information, and said strip being secured to said vial;

a cap having a top and a rim, said cap being adapted to matingly engage said open end of said vial, said cap being adapted to seal said open end of said vial by advancing said cap into a secure position, said cap having a sensing tab that extends over said contact of said electronic memory strip when in said secure position;

a sensor located in said sensing tab of said cap, said sensor being in electrical communication with said contact when in said secure position;

a computer processor located in said cap, said sensor being in electrical communication with said computer processor, and said computer processor using said predetermined information to select desired information; and a communication device located in said cap and in electrical communication with said computer processor, said computer processor communicating said desired information to said communication device, and altering said predetermined information in said electronic memory strip.

35. The medication container of claim 34, and wherein said cap includes a timing device for determining time information, and said predetermined information includes prescribed dosing regimen information and said computer processor uses said time information and said prescribed dosing regimen information to develop a predetermined time, and computer processor communicates said predetermined time to said communication device.

36. The medication container of claim 35, and further comprising an access control device, and said access control device prevents removal of said cap from said vial until said predetermined time occurs.

37. The medication container of claim 36, and wherein said wall of said vial has an outer surface with a plurality of outwardly projecting spaced apart ratchets located proximal said open end, and said rim of said cap has an inner surface with a plurality of inwardly projecting spaced apart hold down lugs, said cap being adapted to matingly engage said open end of said vial by aligning each of said hold down lugs between adjacent ratchets, said cap being adapted to seal against said open end of said container by rotating said cap until said cap reaches a secure position.

38. The medication container of claim 37, and wherein said access control device includes a plunger located in said cap, said plunger being biased between one of said hold down lugs of said cap and one of said adjacent ratchets of said vial when in said secure position, said plunger being sized to prevent said cap from rotating to a releasable position when said plunger is located in a locked position between one of said lugs and one of said adjacent ratchets.

39. The medication container of claim 38, and wherein said plunger is controlled by a solenoid in electrical communication with said computer processor, and said processor activates said solenoid to move said plunger from said locked position to an opened position at a predetermined time.

40. The medication container of claim 34, and further comprising a memory device located in said cap for storing said predetermined information.

41. The medication container of claim 40, and further comprising buttons located in said cap for manually inputting additional information into said memory device in said cap.

42. The medication container of claim 35, and wherein said cap contains a compressible member that biases said cap and vial into sealed engagement when said cap is in said secure position.

43. The medication container of claim 37, and wherein said sensing tab projects from said rim of said cap, and said vial has a guide ring projecting outwardly from said outer surface of said wall and positioned a predetermined distance from said open end of said vial, said guide ring forming an opening adapted to receive said sensing tab, said guide ring and sensing tab cooperating to align said sensor with said memory strip when in said secure position.

44. The medication container of claim 35, and wherein said communication device is an alarm activated by said computer processor when said predetermined time occurs.

45. The medication container of claim 34, and wherein said electronic memory strip includes a contact in electrical communication with said memory strip for accessing said information in said memory strip.

46. The medication container of claim 43, and further comprising a label upon which alphanumeric information is printed, said electronic memory strip being secured to said label.

47. The medication container of claim 46, and wherein said label is located on said outer wall of said container, below said ratchets and aligned with said opening formed by said guide ring.

48. The medication container of claim 34, and wherein said container is substantially cylindrical and said top of said cap is substantially round.

49. The medication container of claim 36, and wherein said electronic memory strip contains a program for processing said predetermined information, said program being communicated to said computer processor when said electronic memory strip is aligned with said sensor of said cap, said program enabling said access control device to permit access to the medication at said predetermined time.

50. The medication container of claim 34, and further comprising means for communicating said predetermined information in said memory strip to a separate computer.

51. A medication container for dispensing doses of medication comprising:

a blister pack formed by a tear resistant molded sheet and a backing sheet, said tear resistant molded sheet having a plurality of pockets, each of said pockets being filled with one of the doses of medication, said backing sheet being secured to said molded sheet and extending over said filled pockets to seal the medication in said pockets;

a dispenser for housing said blister pack, said dispenser having a computer processor;

a machine readable and writable, electronic memory strip containing predetermined information, said electronic memory strip being secured to said blister pack;

a first sensor in electrical communication with said computer processor, said first sensor being in electrical communication with said memory strip when said blister pack is secured to said dispenser, said predetermined information being electrically communicated to said computer processor;

an alignment mechanism for engaging said blister pack and aligning said electronic memory strip with said first sensor, and further aligning one of said filled pockets into a dispensing position;

a plunger aligned with said filled pocket when in said dispensing position;

a dispensing mechanism that advances said plunger into one of said filled pockets to release the medication in said one of said filled pockets; and, a second sensor for sensing the dispensment of the medication from the blister pack, said second sensor being in electrical communication with said computer processor, and said computer processor altering said predetermined information in said electronic memory strip after the medication is dispensed.

52. The medication container of claim 51, and wherein said memory strip contains quantity information regarding the quantity of doses of medication contained in said blister pack, and said computer processor reduces the quantity information when said second sensor communicates that the medication has been dispensed.

53. The medication container of claim 51, and wherein said electronic memory strip contains a program for processing said predetermined information, said program being communicated to said computer processor when said electronic memory strip is aligned with said first sensor of said dispenser.

54. The medication container of claim 53, and wherein said cap includes a timing device for determining time information in electrical communication with said computer processor, said electronic memory strip includes prescribed dosing regimen information, and said computer processor uses said prescribed dosing regimen information and said time information to develop a predetermined time to take the medication.

55. The medication container of claim 54, and further including an access control device that advances said blister pack a predetermined interval to align an adjacent pocket filled with one of the doses of medication into said dispensing position at said predetermined time.

56. The medication container of claim 51, and further comprising a memory device in said dispenser for receiving said predetermined information from said first sensor; said memory device being in communication with said computer processor.

57. The medication container of claim 51, and wherein said electronic memory strip is secured to a substantially flat central area of said blister pack.

58. The medication container of claim 51, and wherein said tear resistant sheet is perforated around each of said pockets to define a discrete portion of said blister pack containing one of the doses of medication, and said perforations facilitating removal of said discrete portion from said blister pack.

59. The medication container of claim 51, and further comprising a protective coating covering predetermined portions of said electronic memory strip.

60. The medication container of claim 51, and further comprising means for communicating said predetermined information in said memory strip to a separate computer.

* * * * *